(12) United States Patent
Sanzol Baztan et al.

(10) Patent No.: US 12,734,200 B2
(45) Date of Patent: Sep. 15, 2026

(54) PROBIOTICS FOR REGULATING BLOOD GLUCOSE

(71) Applicant: GENBIOMA APLICACIONES, S.L., Esquiroz (ES)

(72) Inventors: Gregorio Sanzol Baztan, Pamplona (ES); Miguel Ángel Barajas Vélez, Pamplona (ES); Ignacio José Encío Martínez, Gorraiz (ES); Jesús V. Díaz Cano, Alhama de Murcia (ES); María Oneca Agurruza, Pamplona (ES); Ricardo Sánchez-Valverde Amatriain, Pamplona (ES); Miriam Araña Ciordia, Nuevo Artica (ES); Jorge Sánchez-Valverde Amatriain, Pamplona (ES); Josune Ayo Martínez, Sopelana (ES)

(73) Assignee: GENBIOMA APLICACIONES, S.L., Esquiroz (ES)

( * ) Notice: Subject to any disclaimer, the term of this patent is extended or adjusted under 35 U.S.C. 154(b) by 775 days.

(21) Appl. No.: 17/787,270

(22) PCT Filed: Dec. 18, 2020

(86) PCT No.: PCT/EP2020/087284
§ 371 (c)(1),
(2) Date: Jun. 17, 2022

(87) PCT Pub. No.: WO2021/123355
PCT Pub. Date: Jun. 24, 2021

(65) Prior Publication Data
US 2023/0038352 A1 Feb. 9, 2023

(30) Foreign Application Priority Data
Dec. 20, 2019 (EP) .................................... 19383179

(51) Int. Cl.
*A61K 35/744* (2015.01)
*A61K 31/155* (2006.01)
(Continued)

(52) U.S. Cl.
CPC .......... *A61K 35/744* (2013.01); *A61K 31/155* (2013.01); *A61K 31/716* (2013.01); *A61K 33/24* (2013.01); *A61P 3/10* (2018.01)

(58) Field of Classification Search
CPC .. A61K 35/744; A61K 31/155; A61K 31/716; A61K 33/24; A61K 2035/115;
(Continued)

(56) References Cited

U.S. PATENT DOCUMENTS 9,603,878 B2 * 3/2017 Berry ....................... A61K 9/19
2017/0020929 A1 * 1/2017 Lin et al. ............. A61K 35/744

FOREIGN PATENT DOCUMENTS

CN 107028985 A 8/2017
KR 20130104271 A * 9/2013
(Continued)

OTHER PUBLICATIONS

Cai et al. In vitro evaluation by PCA and AHP of potential antidiabetic properties of lactic acid bacteria isolated from traditional fermented food, LWT—vol. 115, Jul. 29, 2019 (Year: 2019).*
(Continued)

*Primary Examiner* — Sharmila G Landau
(74) *Attorney, Agent, or Firm* — Squire Patton Boggs (US) LLP

(57) ABSTRACT

The present application refers to oral compositions comprising an effective amount of a *Pediococcus acidilactici* strain for use in regulating blood glucose levels, as well as for the prevention and/or treatment of hyperglycemia and/or a hyperglycemia-related condition. The application also refers to *Pediococcus acidilactici* CECT 9879, *Pediococcus aci-*
(Continued)

*dilactici* CECT 9889 and *Pediococcus acidilactici* CECT 9967, and to these strains for use as probiotics, medicaments and for regulating blood glucose levels, as well as for the prevention and/or treatment of hyperglycemia and/or a hyperglycemia-related condition.

8 Claims, 8 Drawing Sheets

(51) Int. Cl.
*A61K 31/716* (2006.01)
*A61K 33/24* (2019.01)
*A61P 3/10* (2006.01)

(58) Field of Classification Search
CPC . A61K 35/742; A61P 3/10; A61P 3/08; C12N 1/20; C12N 1/205; C12R 2001/01
See application file for complete search history.

(56) References Cited

FOREIGN PATENT DOCUMENTS

WO WO2011018580 * 2/2011
WO WO2011018580 A1 * 2/2011

OTHER PUBLICATIONS

Bioactive compound; NCI Dictionary of Cancer Terms. https://www.cancer.gov/publications/dictionaries/cancer-terms/def/bioactive-compound. Last updated 2011, Last accessed Feb. 17, 2025. (Year: 2011).*

Bansal. Prediabetes diagnosis and treatment: A review. World J Diabetes Mar. 15, 2015; 6(2): 290-303. (Year: 2015).*

International Search Report and Written Opinion mailed May 21, 2021 for Application No. PCT/EP2020/087284, 17 pages.

Andrikopoulos, et al: "Evaluating the glucose tolerance test in mice", Am J Physiol Endocrinol Metab; Sep. 23, 2008; vol. 295(6), E1323-1332; doi: 10.1152/ajpendo.90617.2008.

Cai , et al: "In vitro evaluation by PCA and AHP of potential antidiabetic properties of lactic acid bacteria isolated from traditional fermented food", LWT Food Science and Technology; Jul. 29, 2019; vol. 115, 10345S.

"2.9.3. Dissolution test for solid dosage forms", European Pharmacopoeia 6.0., Jan. 2008; pp. 266-275.

Eyth, et al: "Glucose Tolerance Test" [Updated May 25, 2022]. In: StatPearls (Internet). Treasure Island (FL): StatPearls Publishing. Jan. 2022.

Introduction: ADA Standards of Medical Care in Diabetes 2019; American Diabetes Association. Diabetes Care; Jan. 2019; vol. 42(Supplement 1): S1-2; https://doi.org/10.2337/dc19-Sint01.

Muyzer, et al: "Profiling of complex microbial populations by denaturing gradient gel electrophoresis analysis of polymerase chain reaction-amplified genes coding for 16S rRNA", Appl Environ Microbiol.; Mar. 1993; vol. 59(3), pp. 695-700.

Muyzer, et al: "Phylogenetic relationships of *Thiomicrospira* species and their identification in deep-sea hydrothermal vent samples by denaturing gradient gel electrophoresis of 16S rDNA fragments", Arch Microbiol.; Sep. 1995; vol. 164(3), pp. 165-172.

"Pharmacologic Approaches to Glycemic Treatment", Standards of Medical Care in Diabetes 2019; American Diabetes Association. Diabetes Care; Jan. 2019; vol. 42(Supplement 1): S90-S102. https://doi.org/10.2337/dc19-S009.

Sambrook, et al: "Molecular Cloning: A Laboratory Manual", Third Edition, vol. 1, Chapter 13 Mutagenesis; 2001.

Moon, et al., "Lipid-lowering effects of Pediococcus acidilactici M76 isolated from Korean traditional makgeolli in high fat diet-induced obese mice." Nutrients. Mar. 7, 2014;6(3):1016-28. doi: 10.3390/nu6031016. PMID: 24609135; PMCID: PMC3967175.

* cited by examiner

A

B

PROBIOTICS FOR REGULATING BLOOD GLUCOSE

CROSS-REFERENCE TO RELATED APPLICATIONS

The present application is a 35 U.S.C. § 371 national-phase filing of International Application No. PCT/EP2020/087284, filed on Dec. 18, 2020, which claims the benefit of European Patent Application EP19383179.9 filed on 20 Dec. 2019, both of which are incorporated herein by reference in their entirety.

TECHNICAL FIELD

The present invention relates to probiotic compositions for promoting health, in particular compositions comprising probiotics for regulating blood glucose levels.

BACKGROUND ART

Diabetes mellitus, often referred to simply as diabetes, is a condition characterized by disordered metabolism and abnormally high blood sugar (hyperglycemia, also spelled hyperglycemia) resulting from insufficient levels and/or action of the hormone insulin. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy. These symptoms are likely to be less apparent if the blood sugar is only mildly elevated.

Diabetes mellitus presents itself in different forms, being type 1, type 2, and gestational diabetes the main forms. While, ultimately, all forms are due to the beta cells of the pancreas being unable to produce sufficient insulin to prevent hyperglycemia, the causes of the several diabetes forms are different. Type 1 diabetes is usually due to autoimmune destruction of the pancreatic beta cells. Type 2 diabetes is characterized by insulin resistance in target tissues. This causes a need for abnormally high amounts of insulin and diabetes develops when the beta cells cannot meet this demand. Gestational diabetes is similar to type 2 diabetes in that it involves insulin resistance; the hormones of pregnancy can cause insulin resistance in women genetically predisposed to developing this condition.

While Gestational diabetes typically resolves with delivery of the child, other types of diabetes, including types 1 and 2 diabetes are chronic conditions. All types can be treated with insulin, although dietary and other lifestyle adjustments are part of management.

Diabetes can cause many complications, mostly as a result of prolonged hyperglycemia. Serious long-term complications include cardiovascular disease (doubled risk), chronic renal failure, retinal damage (which can lead to blindness), nerve damage (of several kinds), and microvascular damage, which may cause impotence and poor healing of wounds.

Diabetes mellitus is currently a chronic disease, without a cure, and medical emphasis must necessarily be on managing/avoiding possible short-term as well as long-term diabetes-related problems. There is an exceptionally important role for patient education, dietetic support, sensible exercise, self-glucose monitoring, with the goal of keeping blood glucose levels within acceptable bounds.

Therefore, there is a need in the art to provide new strategies for regulating blood glucose levels.

SUMMARY OF INVENTION

The inventors have found that consumption of bacteria of the species *Pediococcus acidilactici* (*P. acidilactici*) has the surprising effect of regulating blood glucose levels, with the consequence that these bacteria are useful for preventing or treating hyperglycemia and/or hyperglycemia-related conditions.

Thus, in first aspect the invention refers to an oral composition comprising an effective amount of a *Pediococcus acidilactici* strain for use in regulating blood glucose levels. This aspect can be alternatively formulated as the use of an oral composition comprising an effective amount of a *Pediococcus acidilactici* strain for the manufacture of a medicament for regulating blood glucose levels. This may be alternatively formulated as a method for regulating blood glucose levels in an animal in need thereof, including a human, comprising administering to said animal in need thereof an effective amount of an oral composition comprising a *Pediococcus acidilactici* strain.

In another aspect, the invention provides an oral composition comprising an effective amount of a *Pediococcus acidilactici* strain for use in the prevention or treatment of hyperglycemia and/or a hyperglycemia-related condition. This aspect can be alternatively formulated as the use of an oral composition comprising an effective amount of a *Pediococcus acidilactici* strain for the manufacture of a medicament for the prevention and/or treatment of hyperglycemia and/or a hyperglycemia-related condition. This may be alternatively formulated as a method for the prevention and/or treatment of hyperglycemia and/or a hyperglycemia-related condition in an animal in need thereof, including a human, comprising administering to said animal in need thereof an effective amount of an oral composition comprising a *Pediococcus acidilactici* strain.

The results as shown in the examples below effectively show that oral administration of *Pediococcus acidilactici* to non-obese diabetic mice (NOD mice) prevent hyperglycemia in such genetically predisposed animals. NOD mice fed a diet supplemented with *Pediococcus acidilactici* showed blood glucose levels significantly lower than the control (non-supplemented) group. Other examples further demonstrate the blood sugar-regulating effect in another animal model for diabetes, the ZDF model (Zucker diabetic and fatty rat). Such results demonstrate that oral administration of a product containing *Pediococcus acidilactici* was able to delay the debut in diabetes.

Advantageously, it has also been found that the strains of the invention are able to effectively regulate blood glucose levels in prediabetic subjects. The examples show that supplementation with the *Pediococcus acidilactici* strains maintain normal blood glucose levels in Balb/c mice fed an hypercaloric diet (in contrast with control animals which quickly developed high blood sugar levels when fed the same diet).

Moreover, as a further advantage of the present invention, the examples below show that the blood sugar-regulating effect of *Pediococcus acidilactici* is present at surprisingly low doses. The glycemic controlling effect of *Pediococcus acidilactici* supplementation in the diet is also maintained over time.

One additional advantage of the present invention is that the blood sugar-regulating effect of *Pediococcus acidilactici* is independent of the food consumption pattern. Known antidiabetics or blood sugar-regulating drugs need to be administered together or close to food ingestion. These drugs are usually designed to avoid post-prandial hyperglycemia. In contrast, the administration regime of the compositions comprising *Pediococcus acidilactici* of the present invention is independent of food ingestion patterns while providing a constant and long-term blood sugar-regulation.

Another aspect of the invention provides a strain of *Pediococcus acidilactici* deposited at the “Colección Española de Cultivos Tipo” (CECT) with identification reference CECT 9889. A further aspect provides a strain of *Pediococcus acidilactici* deposited at the “Colección Española de Cultivos Tipo” (CECT) with identification reference CECT 9879. A further aspect provides a strain of *Pediococcus acidilactici* deposited at the “Colección Española de Cultivos Tipo” (CECT) with identification reference CECT 9967.

The strain of *Pediococcus acidilactici* CECT 9889 of the invention, isolated from cow stool in Navarra region (Spain) and was deposited, according to the Budapest Treaty, on May 9, 2019 in the “Colección Española de Cultivos Tipo” (CECT), by the depositor Pentabiol S.L., sited at Polígono Industrial Noain-Esquiroz, Calle S, Nave 4, 31191 Esquíroz, Navarra (Spain). The strain of received the accession number CECT 9889 after the International Authority of Deposit declared the strain as viable.

The strain of *Pediococcus acidilactici* CECT 9879 of the invention, was also isolated from cow stool in Navarra region (Spain) and was deposited, according to the Budapest Treaty, on May 9, 2019 in the “Colección Española de Cultivos Tipo” (CECT), by the depositor Pentabiol S.L., sited at Polígono Industrial Noain-Esquiroz, Calle S, Nave 4, 31191 Esquíroz, Navarra (Spain). The strain of received the accession number CECT 9879 after the International Authority of Deposit declared the strain as viable.

The strain of *Pediococcus acidilactici* CECT 9967 of the invention, isolated from cow stool in Navarra region (Spain) and was deposited, according to the Budapest Treaty, on Jan. 10, 2019 in the “Colección Española de Cultivos Tipo” (CECT), by the depositor Pentabiol S.L., sited at Polígono Industrial Noain-Esquiroz, Calle S, Nave 4, 31191 Esquíroz, Navarra (Spain). The strain of received the accession number CECT 9967 after the International Authority of Deposit declared the strain as viable.

The depositor Pentabiol S.L. authorised GENBIOMA APLICACIONES, S.L. sited in Polígono Industrial Noain-Esquiroz Calle S, Nave 4, 31191 Esquíroz, Navarra (Spain) to refer to the deposited biological material in the European patent application having the representative’s reference number P5191EP00, and gave his unreserved and irrevocable consent to the deposited material being made available to the public as from the date of filing of this patent application.

A further aspect of the invention refers to a *Pediococcus acidilactici* CECT 9889 strain, a *Pediococcus acidilactici* CECT 9879 strain or a *Pediococcus acidilactici* CECT 9967 strain as defined above for use as probiotic.

In a still further aspect, the invention refers to a *Pediococcus acidilactici* CECT 9889 strain, a *Pediococcus acidilactici* CECT 9879 strain or a *Pediococcus acidilactici* CECT 9967 strain as defined above for use as a medicament.

In this sense, the bacterial strains of the invention have shown advantageous properties, such as good thermal resistance, good long-term stability (shell-life) and post-biotic activity. It is also interesting that the strains of the invention maintain their ability to regulate blood glucose levels even when they are non-viable (inactivated). Moreover, the strains of the invention conveniently grow in different culture media to yield cultures with very high cell density (up to 10<10> cfu/ml) in industrial fermenters without losing their glucose regulating activity. All these features are advantageous for industrial handling and commercial use of the strains, and particularly for use as probiotics or medicaments.

Also, aspects of the present invention refer to a *Pediococcus acidilactici* CECT 9889 strain, a *Pediococcus acidilactici* CECT 9879 strain or a *Pediococcus acidilactici* CECT 9967 strain as defined above for use in regulating blood glucose levels. This aspect can be alternatively formulated as the use of *Pediococcus acidilactici* CECT 9889, *Pediococcus acidilactici* CECT 9879 or *Pediococcus acidilactici* CECT 9967 for the manufacture of a medicament for regulating blood glucose levels. This may be alternatively formulated as a method for regulating blood glucose levels in an animal in need thereof, including a human, comprising administering to said animal in need thereof *Pediococcus acidilactici* CECT 9889, *Pediococcus acidilactici* CECT 9879 or *Pediococcus acidilactici* CECT 9967.

Additional aspects of the present invention refer to a *Pediococcus acidilactici* CECT 9889 strain, a *Pediococcus acidilactici* CECT 9879 strain or a *Pediococcus acidilactici* CECT 9967 strain as defined above for use in in the prevention and/or treatment of hyperglycemia and/or a hyperglycemia-related condition. This aspect can be alternatively formulated as the use of *Pediococcus acidilactici* CECT 9889, *Pediococcus acidilactici* CECT 9879 or *Pediococcus acidilactici* CECT 9967 for the manufacture of a medicament for the prevention and/or treatment of hyperglycemia and/or a hyperglycemia-related condition. This may be alternatively formulated as a method for the prevention and/or treatment of hyperglycemia and/or a hyperglycemia-related condition in an animal in need thereof, including a human, comprising administering to said animal in need thereof *Pediococcus acidilactici* CECT 9889, *Pediococcus acidilactici* CECT 9879 or *Pediococcus acidilactici* CECT 9967.

Another aspect refers to a process for obtaining a viable cell suspension derived from a strain selected from *Pediococcus acidilactici* CECT 9889, *Pediococcus acidilactici* CECT 9879 or *Pediococcus acidilactici* CECT 9967 as defined above, the process comprising: (i) inoculating the *Pediococcus acidilactici* CECT 9889, *Pediococcus acidilactici* CECT 9879 or *Pediococcus acidilactici* CECT 9967 in a culture medium, (ii) subjecting the inoculated culture medium of the step (i) to conditions suitable for growth of the strain, and (iii) optionally subjecting the medium resulting from step (ii) to a concentration step.

Another aspect of the invention refers to a method to obtain a mutant of *Pediococcus acidilactici* CECT 9889, *Pediococcus acidilactici* CECT 9879 or *Pediococcus acidilactici* CECT 9967 comprising the step of subjecting the *Pediococcus acidilactici* CECT 9889, the *Pediococcus acidilactici* CECT 9879 or *Pediococcus acidilactici* CECT 9967 strain to a DNA recombinant technique, for example mutagenesis, or to conditions to generate spontaneous mutations, for example UV light. The mutant contemplated in this aspect of the retains the characteristics and relevant advantages of the strains of the invention, in particular, the ability to regulate blood glucose levels. The mutants usually retain above 99% DNA sequence identity, for example above 99.9% sequence identity, (along the full length of the genome) with the original strain from which it derives. The terms mutant strain or derivative strain can be used indifferently.

The invention also contemplates a mutant of the strain *Pediococcus acidilactici* CECT 9889, *Pediococcus acidilactici* CECT 9879 or *Pediococcus acidilactici* CECT 9967 obtained as defined above having above 99% DNA sequence identity, for example above 99.9% sequence identity, (along the full length of the genome) with the original strain from which it derives and which retains the ability to regulate blood glucose levels of the strain from which it derives.

DETAILED DESCRIPTION OF THE INVENTION

Definitions

Figure 1:
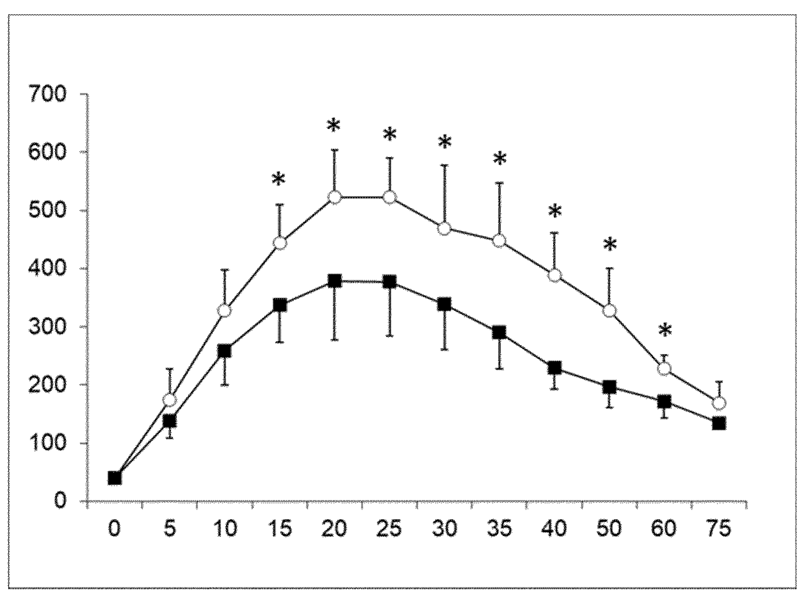
FIG. 1. Glucose tolerance test at week 30. The control group (line with circles, n=6 female NOD mice) showed higher levels of blood glucose after the administration of 4 mg/kg of glucose with respect to the group whose diet was supplemented with a product containing the strain of *Pediococcus acidilactici* 9879 (line with black squares, n=6 female NOD mice). The ordinate axis (Y) represents the glycaemia (mg/dl) and the abscissa axis (X) the time (minutes). Values marked with an asterisk (*) indicate differences with a statistically significant p value (p<0.05).

The term "probiotic" in the sense of the present invention is defined as a microorganism, which upon ingestion in certain amounts, exert health benefits beyond inherent basic nutrition. In the present invention the term "probiotic" includes non-viable microorganisms.

The term "prebiotics" is generally defined as non-digestible food ingredients that beneficially affect the host by selectively stimulating the growth and/or activity of one or a limited number of bacteria in the colon, and thus improve host health. Typically, prebiotics are carbohydrates (such as oligosaccharides), but the definition does not preclude non-carbohydrates.

"Medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need marketing approval, but may include substances which can be used in cosmetics, nutraceuticals, food (including feeds) and natural remedies.

The term "effective amount" as used herein, means an amount of an active agent high enough to deliver the desired benefit, but low enough to avoid serious side effects within the scope of medical judgment. This term refers to that amount of the active component of the pharmaceutical composition which is sufficient to cause the prevention and/or treatment, of a disease or pathological condition of interest in the mammal, particularly in humans. The effective amount could vary according to the activity of the strain of the invention and its active agents, according to its metabolic stability, in any presentation form, and among other factors, but it can be determined by a person skilled in the art according to his/her own knowledge and this description.

In this specification the term "bacterial metabolites" includes all molecules produced or modified by the (probiotic) bacteria as a result of bacterial metabolism during growth, survival, persistence, transit or existence of bacteria during probiotic product manufacture and storage and during gastrointestinal transit in a mammal.

The term "mutants" refer to strains obtained using the bacterial strains of the invention as starting material and characterized by maintaining the herein described blood glucose controlling effects. A "mutant" of the strain is also understood according to the invention as a "variant" or "derivative".

In this specification the term "preventing" refers to preventing the specified condition from occurring in a mammal which may be predisposed to the condition or is exposed to conditions that favor developing of the condition but does not yet experience or display the pathology or symptomatology.

The term "treatment" refers to inhibiting the condition in a mammal that is experiencing or displaying the pathology or symptomatology of the condition (i.e., arresting further development of the pathology and/or symptomatology) or ameliorating the condition in a mammal that is experiencing or displaying the pathology or symptomatology of the condition (i.e., reversing the pathology and/or symptomatology or stopping or slowing its progression).

The "blood glucose level", "blood sugar level", "blood sugar concentration", or simply "glycemia", is the concentration of glucose present in the blood of humans and other animals.

As utilized herein, "regulating blood glucose levels", which could be also worded as "controlling blood glucose levels" refers to any increase, decrease, and/or maintenance in or of the concentration of blood glucose as compared to a previously determined level. In particular embodiments, of the invention the regulating refers to maintaining the blood glucose within normal levels or lowering blood glucose levels that are above the normal threshold, whether it achieves a normal level or not. In other embodiments the "regulating" may refer to restraining a blood glucose concentration that is already higher than normal from being even higher.

"Hyperglycemia" is a condition in which an excessive amount of glucose circulates in the blood plasma. Hyperglycemia is generally understood as fasting blood glucose level over 126 mg/dL "Diabetes mellitus", commonly known as "diabetes", is a group of metabolic disorders characterized by high blood sugar levels over a prolonged period. Symptoms of high blood sugar include frequent urination, increased thirst, and increased hunger. [2] If left untreated, diabetes can cause many complications. Acute complications can include diabetic ketoacidosis, hyperosmolar hyperglycemic state, or death. Serious long-term complications include cardiovascular disease, stroke, chronic kidney disease, foot ulcers, and damage to the eyes. Diabetes is due to either the pancreas not producing enough insulin, or the cells of the body not responding properly to the insulin produced. In the sense of the present invention, "diabetes" includes all forms of diabetes.

"Prediabetes" is generally understood as the precursor stage before diabetes mellitus in which not all of the symptoms required to diagnose diabetes are present, but blood sugar is abnormally high. This stage is often referred to as the "grey area".

As used herein, the term "functional food" means food which is capable of providing not only a nutritional effect, but is also capable of delivering a further beneficial effect to consumer. Accordingly, functional foods are ordinary foods that have components or ingredients (such as those described herein) incorporated into them that impart to the food a specific functional—e.g. medical or physiological benefit—other than a purely nutritional effect. In the sense of the present invention the term food or functional food includes solid foods as well as beverages.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

Bacteria

The bacteria described in the present invention for their surprising effect in controlling blood glucose levels particularly belong to the species *Pediococcus acidilactici*. This species is generally recognized as safe (GRAS) and thus approved for animal and human consumption.

The bacterium may be used in any form capable of exerting the effects described herein. For example, the bacteria may be viable, dormant or non-viable (inactivated or dead bacteria). In one particular example, the bacteria are viable bacteria. In another particular example the bacteria are inactivated.

The bacteria may comprise whole bacteria or may comprise bacterial components. Examples of such components include bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins. For example, the bacteria may comprise lysed bacteria. The bacteria may also or alternatively comprise bacterial metabolites. Examples of bacterial metabolites include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a *sulphurous* acid. In one embodiment the bacteria comprise whole bacteria. In another embodiment the bacteria comprise whole viable bacteria.

In some embodiments of the present invention the bacterial strain is *Pediococcus acidilactici* CECT 9889. In other embodiments the bacterial strain is *Pediococcus acidilactici* CECT 9879. In other embodiments the bacterial strain is *Pediococcus acidilactici* CECT 9967. *Pediococcus acidilactici* CECT 9889, CECT 9967 and CECT 9879 have surprising blood glucose regulating effects when administered in animal models.

An expert in the art will understand that using the bacterial strains of the invention as starting material it is routinely possible to obtain, for example by spontaneous mutation or directed mutagenesis, mutants that retain the characteristics and relevant advantages of the strains of the invention. The present disclosure thus additionally contemplates mutants of the bacteria of the invention, particularly, mutants from the strains *Pediococcus acidilactici* CECT 9889, *Pediococcus acidilactici* CECT 9879 and *Pediococcus acidilactici* CECT 9967. Methods for obtaining mutants of a given bacterial strain are well known in the art. Examples can be found in (Sambrook, J. and Russell, D W "Molecular Cloning: A Laboratory Manual", Chapter 13, "Mutagenesis", Cold Spring Harbor, 3rd Ed., 2001). Mutants may be obtained by genetic engineering methods, such as site directed mutagenesis. Mutants may also be obtained by subjecting the strains of the invention to mutagenic conditions, such as UV light, or to stress conditions, which may result in obtaining what is usually called "spontaneous mutants".

Mutants obtained by the above methods may provide new strains derived from the strains of the invention and having a DNA sequence identity along the whole length of the genome above 98% with respect to the strain from which they derive. Particularly, identity of the obtained mutants to the original strains is above 99%, or above 99.5%, or above 99.9%. Such mutant strains, which retain the characteristics and relevant advantages of the strains of the invention are also for use in regulating blood glucose levels. Thus, all the aspects and embodiments described above or below also apply to said mutants.

Culture

The bacteria of the invention may be obtained as described above by a process of preparing a viable bacterial cell suspension that comprises: (i) inoculating the bacterial strain of the invention in a culture medium, (ii) subjecting the inoculated culture medium of the step (i) to conditions suitable for growth of the strain, and (iii) optionally subjecting the medium resulting from step (ii) to a concentration step.

Non-limiting conditions suitable for the growth of the bacteria of the invention may be as follows. The bacteria of the invention can be cultured on a substrate that may be a liquid broth or solid culture medium, for example in agar plates, using standard culture medium such as Tryptic Soy Agar (TSA), Tryptic Soy Broth (TSB), Man, Rogosa and Sharpe (MRS) agar or broth. Particularly, the culture to be inoculated is in an exponential growth phase close to the stationary phase. Cell multiplication is usually allowed to reach exponential phase, achieving a cell density from 7×10<8> to 2×10<10> colony forming units (CFU)/mL or g substrate. Suitable conditions for the growth of the bacteria are temperatures between 3° and 40° C., for example 35-38° C., for example 37° C., and aerobic conditions or microaerophilic conditions (5% of $CO_2$). An example of the detailed procedure for obtaining cells of the bacteria of the invention in liquid medium is set forth in Example 4. Advantageously, the strains of the invention grow to high cell densities in industrial scale several culture media, including lactose-free media and other allergen-free media.

Suitable concentration techniques for the cell suspension obtained as described above are known to the skilled person and may include centrifugation or filtration of the culture. The skilled person may apply the concentration technique to a desired extend such that a concentrated suspension in the culture medium may be obtained or, if desired, the culture medium may be completely removed. By centrifuging the culture, for example, at a minimum of 9000 g, cells may be separated from the culture medium (supernatant). The cell suspension, concentrated cell suspension or cells may then be used directly, resuspended to a desired density, subjected to dehydration or lyophilization. Washing steps may be introduced when required.

Optionally, the bacterial cells or cell suspensions obtained by the methods defined above may be subjected to a dehydration process. The dehydration can be carried out by a lyophilization process, but the slurry can also be dried by fluidized bed drying, or by atomization. Cryoprotectants and/or lyophilization additives are often added.

The cells may be also be directly frozen or stored as cryoballs. Preservatives such as glycerol are often used when freezing in order to avoid damage to the bacterial cells.

The present application considers directly using the cell suspension obtained as defined above (i.e. the bacterial cells together with the culture medium), the bacterial cells devoid of the culture medium or even the culture medium after removing the bacterial cells (usually called de culture's supernatant). The culture's supernatant contains metabolites secreted by the bacterial cells during their growth which may have strong glucose-regulating effects. Said metabolites may be identified, for example, by HPLC. Moreover, the present application also contemplates using the bacterial cells in a disrupted form, for example, lysed bacterial cells, or even a cell free extract resulting from disrupting the cells and removing cell wall and cell membrane components. The culture's supernatant or bacterial cell free extract may also be concentrated, for example by ultrafiltration or centrifugation, to enrich said medium or extract in desired metabolites.

Therefore, particular embodiments refer to a culture's supernantant of the bacterial strains of the invention. Said culture's supernantant may be obtainable by culturing the bacterial strains as defined above and removing the bacterial cells, for example, by centrifugation. Other particular embodiments refer to a cell free extract of the bacterial strains of the invention. Said cell free extract may be obtainable by subjecting the bacterial cells to disruption, for example, by means of a French press, and removing the cell wall and membrane components, for example by centrifugation.

The cell suspension, bacterial cells, cell free extract or culture's supernatant may be used directly for consumption, for example oral consumption, or may be used as an ingredient for preparing a product (for example, an oral composition such as a food or feed product). The cell suspension or cells may also be used as an inoculum to prepare cultures of the strains of the invention. Therefore, another aspect refers to an inoculum comprising the bacteria of the invention, for example *Pediococcus acidilactici* CECT 9889, *Pediococcus acidilactici* CECT 9879 or *Pediococcus acidilactici* CECT 9967.

Subjects/Medical Indications

The bacteria to which the present invention relates, such as *Pediococcus acidilactici* strain CECT 9889, CECT 9967 or CECT 9879, are administered to a mammal, including for example livestock (including cattle, horses, pigs, sheep), and humans. In some embodiments the mammal is a companion animal (including pets). In other embodiments the subject may suitably be a human. In other embodiments the subject is a livestock animal which is not a mammal, for example poultry or fish.

The bacteria of the invention as shown in the examples below have shown a surprising ability to regulate blood glucose levels. In this sense, the examples below effectively demonstrate that supplementation with *Pediococcus acidilactici* has a beneficial effect in blood sugar levels in several animal models. It has been shown that supplementation with strains of this species results in lower blood sugar concentration and increased survival in animal models when compared with non-supplemented animals. Therefore, the bacteria of the invention are suitable for use in the prevention and/or treatment of hyperglycemia or a hyperglycemia-related disorder.

The skilled person will know what is regarded as "normal" blood glucose levels and when a subject is considered to have hyperglycemia. In general terms, "Normal blood glucose levels" or "normoglycemia" are regarded to be in the range from 70 to 126 mg/dL (3.9 to 7.1 mmol/L) (as measured by a fasting blood glucose test, for example ADA Standards of Medical Care Diabetes Care 2019 January; 42 (Supplement 1): S1-S2. High blood glucose levels are generally considered as fasting blood glucose levels over 112 mg/dL). Hyperglycemia is generally understood as fasting blood glucose level over 126 mg/dL). Blood glucose levels may be determined by methods well known and accessible to the skilled person, for example by monitoring blood glucose levels using ADA 2019 or blood glucose strips on Accu-Chek Aviva (Roche) blood glucometer.

Hyperglycemia-related disorders are, for example, impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

A subject having sustained fasting blood glucose above 126 mg/dl (7 mmol/L) is generally held to have diabetes. For diabetics, glucose levels that are considered to be too hyperglycemic can vary from person to person, mainly due to the person's renal threshold of glucose and overall glucose tolerance.

It is generally understood that impaired glucose tolerance is defined as two-hour glucose levels of 140 to 199 mg per dL (7.8 to 11.0 mmol/L) on the 75-g oral glucose tolerance test. IGT may precede diabetes mellitus by many years and is also a risk factor for mortality.

The bacteria of the invention are then suitable for administering to subjects that have hyperglycemia, are at risk of having hyperglycemia (either by genetic predisposition or because of being exposed to external factors that may induce hyperglycemia such as high carbohydrate diet, hypercaloric diet, insufficient exercise, etc), have IGT or are in risk of having IGT, or have or are in risk of developing an hyperglycemia-related disorder, in particular, diabetes. Subjects that may particularly benefit from receiving the bacteria of the invention are prediabetic subjects.

In some embodiments, administering the bacteria or the composition of the invention maintains normoglycemia in a subject. In some embodiments, administering the bacteria or the composition of the invention reduces hyperglycemia in a subject. In particular embodiments, the reduction if hyperglycemia in the subject is by at least 20% relative to a control. In some embodiments the reduction of hyperglycemia is by at least 30%, or by at least 40%, or by at least 50%, or by at least 55%, or by at least 60%, or by at least 65%, or by at least 70%, or by at least 75%, or by at least 80%, or by at least 85%, or by at least 90%, or by at least 95%, or by 100%, relative to a control. In one embodiment, administering the bacteria or the composition of the invention reduces hyperglycemia in a subject by as much as 100%, or by as much as 110%, or by as much as 120%, relative to a control. In some embodiments administering the bacteria or the composition of the invention reduces hyperglycemia in a subject by 40% to 120%, or by 50 to 120%, or by 60 to 120%, or by 70 to 120%, or by 80 to 120%, or by 90 to 120%, or by 100 to 120%, or by 50 to 100%, or by 60 to 100% or by 70 to 100% or by 80 to 100% or by 90 to 100%, with respect to a control. In some embodiments, the subject has or is suspected of having a hyperglycemia-related disorder, for example type 2 diabetes or prediabetes. In some embodiments the subject is ingesting an hypercaloric diet. In some embodiments the subject is predisposed to having hyperglycemia. In some embodiments, administering the bacteria or the composition of the invention reduces hyperglycemia induced by hypercaloric diet in a subject relative to a control. In some embodiments, the control is the subject before administering of the bacteria or composition of the invention. In some embodiments, the control is another subject that is not administered the bacteria or composition. In a particular embodiment the subject is predisposed to having hyperglycemia and is ingesting an hypercaloric diet and the control is the same subject before administration of the bacteria or composition of the invention or another subject predisposed to hyperglycemia that is ingesting the same hypercaloric diet and is not being administered the bacteria or composition of the invention. Hyperglycemia is generally determined, as mentioned above, by fasting blood glucose level.

In one embodiment, administering the bacteria or the composition of the invention reduces blood glucose levels in a glucose tolerance test by at least 10%, or by at least 15% or by at least 20% or by at least 25% or by at least 30%. In one embodiment, administering the bacteria or the composition of the invention reduces blood glucose levels in a glucose tolerance test by as much as 15%, or by as much as 20%, or by as much as 25%, or by as much as 30%, or by as much as 35%, or by as much as 40%, or by as much as 45%, or by as much as 50%, or by as much as 55%, or by as much as 60%, or by as much as 70%, or by as much as 80%, or by as much as 90%, or by as much as 100%. In some embodiments administering the bacteria or the composition of the invention reduces blood glucose levels in a glucose tolerance test by 10% to 70%, or by 10 to 50%, or by 10 to 40%, or by 15 to 50%, or by 20 to 50%, or by 15 to 30%.

The blood glucose tolerance test may be performed by methods well known in the art (for example, Andrikopoulos et al., 2008; Eyth et al., 2019). Fasting blood glucose levels can also be determined by well known methods (see above).

In some embodiments, the maintaining normoglycemia, the reducing hyperglycemia or the reducing blood glucose level in a glucose tolerance test, is achieved by administering a daily dose comprising bacterial cells of the invention in an amount from 10<8> to 10<11> (alone or in a composition) during at least 1 to 4 weeks. In particular embodiments the daily dose is administered during at least 1 to 2 weeks. In particular embodiments the daily dose comprises bacterial cells of the invention in an amount from 10<9> to 10<10>.

Dosage

The bacteria of the invention (such as a strain of *Pediococcus acidilactici*, for example *Pediococcus acidilactici* CECT 9889, CECT 9967 or CECT 9879), used in accordance with the present invention may be administered on or in a support comprising from 10<4> to 10<12> bacteria/g of support, and more particularly from 10<4> to 10<11> bacteria/g of support, particularly 10<4> to 10<9> bacteria/g of support, for example 10<4>, 10<5>, 10<6>, 10<7>, 10<8> or 10<9> bacteria/g of support. The amount of bacteria per unit may be determined by methods known in the art. The bacteria may be viable bacteria, and may then be expressed as CFU, which stands for colony-forming units. However, the bacteria may also be non-viable, as it has been surprisingly found that the bacteria of the invention maintain their ability to regulate glucose levels when they are not viable. When referring to "bacteria" it is understood bacterial cells. By support is meant the food product, dietary supplement or the pharmaceutically acceptable support. When the support is a liquid support then the amount of bacteria is per mL of support.

Suitably, the bacteria of the invention (such as a strain of *Pediococcus acidilactici*, for example *Pediococcus acidilactici* CECT 9889, CECT 9967 or CECT 9879), used in accordance with the present invention, may be administered at a dosage of from about 10<4> to about 10<12> bacteria/dose. By the term "per dose" it is meant that this amount of bacteria is provided to a subject either per day or per intake, particularly per day. For example, if the bacteria is to be administered in an oral composition (such as a food supplement or food product, for example in a yoghurt)—then the oral composition will particularly contain from about 10<4> to 10<12> bacterial cells. Alternatively, however, this amount of bacteria may be split into multiple administrations each consisting of a smaller amount of microbial loading-so long as the overall amount of bacteria received by the subject in any specific time (for instance each 24-hour period) is from about 10<4> to about 10<12> bacteria. The dosage may particularly be from about 10<4> to 10<11> bacteria/dose, and in certain embodiments it may be from about 10<4> to 10<10> bacteria/dose, or from about 10<4> to 10<9> bacteria/dose, or from about 10<4> to 10<7> bacteria/dose, or from about 10<4> to 10<6> bacteria/dose, or from about 10<5> to 10<8> bacteria/dose, or from 10<8> to 10<11> bacteria/dose, or from 10<9> to 10<10> bacteria/dose. The dosage may be 10<4>, 10<5>, 10<6>, 10<7>, 10<8>, 10<9>, 10<10> or 10<11> bacteria/dose.

In one embodiment, the bacteria of the invention, for example a *Pediococcus acidilactici*, such as *Pediococcus acidilactici* CECT 9889, CECT 9967 or CECT 9879, may be administered at a dosage of from about 10<4> to 10<12> bacteria/day, or from about 10<4> to 10<10> bacteria/day, or from about 10<5> to 10<9> bacteria/day, or from about 10<4> to 10<9> bacteria/day, or from about 10<4> to 10<7> bacteria/day, or from about 10<4> to 10<6> bacteria/day, or from about 10<5> to 10<8> bacteria/day, or from 10<8> to 10<12> bacteria/day, or from 10<9> to 10<10> bacteria/day, for example 10<4>, 10<5>, 10<6>, 10<7>, 10<8>, 10<9>, 10<10>, or 10<11> bacteria/day.

When the bacteria, such as a strain of *Pediococcus acidilactici*, for example *Pediococcus acidilactici* CECT 9889, CECT 9967 or CECT 9879, are used in the present invention together with other species, the bacteria may be present in any ratio capable of achieving the desired effects of the invention described herein. Typically, the *Pediococcus acidilactici* to each other or other species ratio (measured in terms of colony forming units) is in the range 1:100 to 100:1, suitably 1:50 to 50:1, particularly 1:20 to 20:1, more particularly 1:10 to 10:1, still more particularly 1:5 to 5:1, yet more particularly 1:3 to 3:1 and even more particularly 1:2 to 2:1 and most particularly 1:1.5 to 1.5:1.

Compositions and Combinations

While is it possible to administer the bacteria according to the present invention alone (i.e. without any support, diluent or excipient), the bacteria are typically administered on or in a support as part of a composition. The composition may be, for example, an oral, parenteral, rectal, vaginal, topical, intradermal, transdermal, subcutaneous, sublingual, intravenous or nasopharyngeal composition. In one embodiment, the composition of the invention is an oral composition. In particular embodiments, the oral composition of the invention comprises a bacteria of the invention, in particular a *Pediococcus acidilactici* strain, for example *Pediococcus acidilactici* CECT 9889, CECT 9967 or CECT 9879. In some embodiments the oral composition comprises *Pediococcus acidilactici* CECT 9889.

In other embodiments, the oral composition comprises *Pediococcus acidilactici* CECT 9879. In other embodiments, the oral composition comprises *Pediococcus acidilactici* CECT 9967. In other embodiments, the oral composition comprises a combination of *Pediococcus acidilactici* CECT 9889 and *Pediococcus acidilactici* CECT 9879. In other embodiments, the oral composition comprises a combination of *Pediococcus acidilactici* CECT 9889 and *Pediococcus acidilactici* CECT 9967. In other embodiments, the oral composition comprises a combination of *Pediococcus acidilactici* CECT 9879 and *Pediococcus acidilactici* CECT 9967. In other embodiments, the oral composition comprises a combination of *Pediococcus acidilactici* CECT 9889, *Pediococcus acidilactici* CECT 9879 and *Pediococcus acidilactici* CECT 9967.

In particular embodiments, the oral composition of the invention is such as a food product, food ingredient, food supplement, a pharmaceutical product or a nutraceutical product. These products typically contain additional components well known to those skilled in the art. The amount of bacteria of the invention present in the oral compositions is according to what has been described above.

In one embodiment, bacteria of the invention, in particular, the *Pediococcus acidilactici*, such as strains CECT 9889, CECT 9967 or CECT 9879, are employed according to the invention in a food product. Here, the term food is used in a broad sense- and covers food for humans as well as food for animals (i.e. a feed). In a particular embodiment, the food is for human consumption. In another particular embodiment, the food is for a non-human animal consumption (feed), in particular for pets or livestock (including fish).

In particular embodiments, the oral composition of the invention is a functional food. In other embodiments the oral composition of the invention is a nutraceutical. In other embodiments the oral composition of the invention is a pharmaceutical composition.

The composition of the present invention may also be used as—or in the preparation of—a pharmaceutical or nutraceutical. Here, the term pharmaceutical or nutraceutical is used in a broad sense—and covers pharmaceuticals or nutraceuticals for humans as well as pharmaceuticals or nutraceuticals for animals (i.e. veterinary applications). In a preferred aspect, the pharmaceutical or nutraceutical is for human use and/or for animal husbandry. When used as—or in the preparation of—a pharmaceutical or nutraceutical composition, the composition of the present invention may be used in conjunction with one or more of: a (pharmaceutically) acceptable excipients or carriers.

The composition of the invention may be presented in any dosage form, for example, solid or liquid, and can be administered by any suitable route. In particular embodiments the pharmaceutical or nutraceutical compositions of the invention are oral compositions (compositions for oral administration). Compositions provided herein suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles.

The tablets, capsules, and other solid dosage forms of the pharmaceutical compositions described herein, such as dragees, pills and granules, may optionally be scored or prepared with coatings and shells, such as enteric coatings and other coatings well known in the art. They may also be formulated so as to provide slow or controlled release of the active ingredient using, for example, hydroxypropylmethyl cellulose in varying proportions to provide the desired release profile, other polymer matrices, liposomes and/or microspheres. Compositions described herein may also be formulated for rapid release, e.g., freeze-dried. These compositions may be formulated to release the active ingredient (s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Non-limiting examples of acceptable excipients are microcrystalline cellulose, lactose, sodium citrate, calcium carbonate, dibasic calcium phosphate and glycine; disintegrants such as starch, sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc; cryoprotectants, such as DMSO, ethylene glycol, glycerol, 2-Methyl-2,4-pentanediol (MPD), propylene glycol, sucrose and trehalose. Examples of pharmaceutically acceptable carriers include, for example, water, salt solutions, alcohol, silicone, waxes, petroleum jelly, vegetable oils, polyethylene glycols, propylene glycol, liposomes, sugars, gelatin, starch, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

The compositions of the invention may also contain a preservative. Examples of preservatives may include antioxidants, chelating agents, antimicrobial preservatives, antifungal preservatives, alcohol preservatives, acidic preservatives, and other preservatives. The compositions of the invention may also contain an antioxidant. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. The compositions of the invention may also contain a chelating agent. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. The compositions of the invention may also contain a buffering agent. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

In one embodiment the composition comprises a lubricant and a bulking agent. the composition of the invention comprises an lubricant, for example, magnesium stearate. The amount of lubricant in the composition may be from 0.1 to 5% of the total composition, or from 0.5 to 2% of the total composition or from 0.5 to 1.5% of the total composition. In another embodiment, the composition comprises a bulking agent, for example selected from cellulose, starch and combinations thereof. The cellulose may be for example microcrystalline cellulose. The starch may be for example corn starch. The amount of bulking agent in the composition may be from 30 to 90% of the total composition, or from 40 to 80% of the total composition, or from 50 to 80% of the total composition, or from 30 to 50% of the total composition, or from 40 to 60% of the total composition. In another particular embodiment the composition comprises a cryoprotectant, for example, sucrose, glycerol or trehalose. The amount of cryoprotectant in the composition may be from 0.5 to 20% of the total composition, or from 1 to 10% of the total composition. In a particular embodiment the composition comprises microcrystalline cellulose, starch and magnesium stearate. In a particular embodiment the composition further comprises a cryoprotectant. In a particular embodiment the bacteria in the composition is of the species *Pediococcus acidilactici*, for example *Pediococcus acidilactici* CECT 9889, CECT 9967 or CECT 9879, particularly, *Pediococcus acidilactici* CECT 9879. By "% of the total composition" is understood herein as % by weight when the composition is solid or % by volume when the composition is liquid. In several embodiments the % is understood as % weight of component/weight of total composition.

In some embodiments, the composition of the invention, for example, the oral composition, comprising a *Pediococcus acidilactici* strain, such as *Pediococcus acidilactici* CECT 9889, CECT 9967 or CECT 9879, or mixtures thereof, may further comprise, or may be for use in combination with, a further active ingredient. Said further active ingredients are selected, in particular embodiments, from prebiotics and other bioactive compounds which have blood glucose regulating effects. In particular embodiments the composition additionally comprises a prebiotic. In other particular embodiments the composition additionally comprises other bioactive compounds that reduce post-prandial glycemic responses or that contributes to the maintenance of normal blood glucose levels.

Examples of suitable prebiotics include complex carbohydrates, complex sugars, resistant dextrins, resistant starch, amino acids, peptides, nutritional compounds, biotin, polydextrose, oligosaccharides, polysaccharide, fructooligosaccharide (FOS), fructans, soluble fiber, insoluble fiber, fiber, starch, galactooligosaccharides (GOS), inulin, lignin, psyllium, chitin, chitosan, gums (e.g. guar gum), high amylose cornstarch (HAS), cellulose, b-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, resistant starch, xylooligosaccharides (XOS), locust bean gum, P-glucan, and methylcellulose. Prebiotics can be found in foods (e.g. acacia gum, guar seeds, brown rice, rice bran, barley hulls, chicory root, Jerusalem artichoke, dandelion greens, garlic, leek, onion, asparagus, wheat bran, oat bran, baked beans, whole wheat flour, banana), and breast milk. In particular embodiments the the prebiotic is selected from galacto-oligosaccharide (GOS), fructo-oligosaccharide (FOS), inulin, alginate, xanthan, pectin, locust bean gum (LBG), guar gum, polydextrose (i.e. Litesse®), resistant starch, hydroxypropyl methylcellulose, beta-glucans (derived from example from barely and oat) and arabinoxylan.

The bioactive compounds used in the combination may be selected from sugar replacers, normoglycemic agents and drugs that control blood sugar levels.

Non-limiting sugar replacers which are suitable for use in the combination of the invention are xylitol, sorbitol, mannitol, maltitol, lactitol, isomalt, erythritol, D-tagatose, isomaltulose, sucralose or polydextrose, soybean oligosaccharides, isomaltulose (Palatinose™), isomalto-oligosaccharides, gluco-oligosaccharides, xylo-oligosaccharides, manno-oligosaccharides, lactitol, lactosucrose and fructose.

Non-limiting normoglycemic agents which are suitable for use in the combination of the invention are fructo-oligosaccharide (FOS), inulin, resistant starch, oat and barely beta-glucans, xylitol, sorbitol, mannitol, maltitol, lactitol, isomalt, erythritol, D-tagatose, isomaltulose, sucralose or polydextrose, berberine (main active component of an ancient Chinese herb Coptis chinensis French) and other forms of berberine (Berberine hydrochloride), Avocatin B (fatty acids avocadene and avocadyne and their metabolites), beta-ecdysterone, maqui berry extract (Delphinol®), clove derived polyphenols (Clovinol®), cinnamon extract (CinSulin®), polyphenols from brown seaweeds (InSea2®), natural phenol as resveratrol, flavonoid group of polyphenols as quercetin, gamma linolenic acid (GLA), chromium and other forms of chromium (chromium picolinate, Crominex® 3+, etc), polyphenols, antocianidyns and delphinins, dietary fibers from bamboo shoot shell, Gamma Cyclodextrin, Omega-6 fatty acids, linoleic acid, Guava polysaccharides, zinc, zein, resistant starch, arabinoxylans from wheat, beta-glucans (for example derived from oat or bareley), hydroxypropylmethyl cellulose, pectins, xilitol, sorbitol, manitol, maltitol, lactitol, isomaltose, erythritol, sucralose y polydextrose, D-tagatose, isomaltulose, $\alpha$-ciclodextrin, fructose, non-digestible hydrocarbons, galacto-oligosaccharide (GOS), in particular alpha-GOS, resistant dextrin, corn stach with high amylose content, corn starch with migh amylose content and Psyllium husk.

Non-limiting examples of drugs that control blood sugar levels which may be used in such a combination include insulin, insulin analogs, biguanides (such as metformin), sulfonylureas (such as carbutamide, chlorpropamide, glibenclamide (Glyburide™), gliclazide, glimepiride, glipizide, gliquidone, tolazamide or tolbutamide), alpha-glucosidase inhibitors (such as acarbose, miglitol or voglibose), thiazolidinediones (TZD) (such as pioglitazone, rivoglitazone or rosiglitazone), meglitinides (such as nateglinide, repaglinide or mitiglinide), dipeptidyl peptidase-4 (DPP-4) inhibitors (such as alogliptin, saxagliptin, sitagliptin or vildagliptin), glucagon-like peptide-1 analogs (such as exenatide, liraglutide, or albiglutide), amylin analogs (such as pramlintide), fast acting insulin analogs (such as insulin lispro, insulin aspart and insulin glulisine), long acting insulin analogs (such as insulin glargine, insulin detemir), dual PPAR agonists (such as aleglitazar) and SGLT2 inhibitors (such as dapagliflozin, remogliflozin and sergliflozin), metformin, α-glucosidase inhibitors, meglitinides, thiazolidinediones, sulphonylureas, biguanidesand acarbose. In one embodiment, the bacteria, compositions or combinations defined above may be used according to the present invention in combination with one or more antidiabetic drug.

The dosage, mode of administration and formulation of the above antidiabetic drugs in the composition of the invention or for use in the combination of the present invention will be readily apparent to a skilled person. In a particular embodiment the bacteria in the combination is of the species *Pediococcus acidilactici*, for example CECT 9889, CECT 9967 or CECT 9879, more particularly *Pediococcus acidilactici* CECT 9879, and the antidiabetic drug will be applied according to the stage of the disease, as specified by the ADA (Pharmacologic Approaches to Glycemic Treatment: Standards of Medical Care in Diabetes-2019; American Diabetes Association. Diabetes Care 2019 January; 42 (Supplement 1): S90-S102.

In one embodiment, the bacteria, compositions or combinations defined above may be used according to the present invention in combination with both a prebiotic (as described above) and an antidiabetic drug (as described above).

Particularly, the bacteria in the combination or the composition (with a prebiotic, bioactive compounds that reduce post-prandial glycemic responses, other bioactive compounds that contributes to the maintenance of normal blood glucose levels, an antidiabetic drug, or combinations thereof) is of the species *Pediococcus acidilactici*, more for example *Pediococcus acidilactici* CECT 9889, CECT 9967 or CECT 9879 and, more particularly, *Pediococcus acidilactici* CECT 9879. Suitably, the prebiotic used in the combination is selected from those described above. Suitably, the bioactive compounds used in the composition or combination is selected from those defined above. Suitably, the antidiabetic used in the composition or combination could be selected from those defined above. In particular embodiments the composition of the invention additionally comprises chromium picolinate.

In a particular embodiment, the bacteria used in the combination is *Pediococcus acidilactici* CECT 9879, the prebiotic is selected from FOS, GOS, inulin, beta-glucan and combinations thereof and the antidiabetic is applied according to the stage of the disease, as specified by the ADA (Diabetes Care 2019 January; 42 (Supplement 1): S90-S102, supra). In particular embodiments the composition, for example oral composition, of the invention additionally comprises or is for use in combination with another microorganism, for example another bacterial strain. Said additional microorganism may be such that it also has blood glucose-regulating effect and may be suitably selected from a strain from *Lactobacillus, Lactococcus, Bacillus, Bifidobacterium, Enterococcus, Saccharomyces*. In one embodiment, the composition, for example oral composition, of the invention additionally comprises or is for use in combination with a strain of *Bacillus licheniformis*. The *Bacillus licheniformis* strain may be *Bacillus licheniformis* deposited at the "Colección Española de Cultivos Tipo" (CECT) with identification reference CECT 9968.

The present invention contemplates any combination of the herein disclosed strains, in particular, combinations of *Pediococcus acidilactici* CECT 9889, CECT 9967 or CECT 9879, or mixtures thereof with one or more of the microorganism with blood glucose-regulating effect defined above, for example *Bacillus licheniformis* CECT 9968. In one embodiment the *Pediococcus acidilactici* in the combination is CECT 9889. In another embodiment the *Pediococcus acidilactici* in the combination is CECT 9879. In another embodiment the *Pediococcus acidilactici* in the combination is CECT 9967. In another embodiment, the combination with another glucose regulating microorganism, for example with *Bacillus licheniformis* CECT 9968, comprises *Pediococcus acidilactici* CECT 9889 and *Pediococcus acidilactici* CECT 9879. In other embodiments, the combination with another glucose regulating microorganism, for example with *Bacillus licheniformis* CECT 9968, comprises *Pediococcus acidilactici* CECT 9889 and *Pediococcus acidilactici* CECT 9967. In other embodiments, the combination with another glucose regulating microorganism, for example with *Bacillus licheniformis* CECT 9968, comprises *Pediococcus acidilactici* CECT 9879 and *Pediococcus acidilactici* CECT 9967. In other embodiments, the combination with another glucose regulating microorganism, for example with *Bacillus licheniformis* CECT 9968, comprises *Pediococcus acidilactici* CECT 9889, *Pediococcus acidilactici* CECT 9879 and *Pediococcus acidilactici* CECT 9967.

The combinations may be administered simultaneously, sequentially or within a certain amount of time. When administered simultaneously the bacteria in the combination may be in the same composition or in different compositions which are administered at the same time.

The present application also provides a strain *Bacillus licheniformis* deposited at the "Colección Española de Cultivos Tipo" (CECT) with identification reference CECT 9968. The strain *Bacillus licheniformis* CECT 9968 was also isolated from cow stool in Navarra region (Spain) and was deposited, according to the Budapest Treaty, on Jan. 10, 2019 in the "Colección Española de Cultivos Tipo" (CECT), by the depositor Pentabiol S.L., sited at Polígono Industrial Noain-Esquiroz, Calle S, Nave 4, 31191 Esquíroz, Navarra (Spain). The strain of received the accession number CECT 9968 after the International Authority of Deposit declared the strain as viable.

*Bacillus licheniformis* CECT 9968 has been found to have blood glucose-regulating effects as shown in example 3.3. The present disclosure thus also considers *Bacillus licheniformis* CECT 9968 for use as probiotic, medicament, in regulating blood glucose levels, as well as for the prevention and/or treatment of hyperglycemia and/or a hyperglycemia-related condition. Further, all features and embodiments disclosed above for the bacteria of the invention, in particular for the *Pediococcus acidilactici* strains of the invention, regarding the bacteria, the subjects, the indications, the culture, the dosage, the compositions, the products and combinations also apply to *Bacillus licheniformis* CECT 9968.

For reasons of completeness, various aspects of the invention are set out in the following numbered embodiments:

Embodiment 1. A *Pediococcus acidilactici* strain for use in regulating blood glucose levels.

Embodiment 2. A *Pediococcus acidilactici* strain for use in the prevention and/or treatment of hyperglycemia and/or a hyperglycemia-related condition.

Embodiment 3. The strain for use according to embodiment 2, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 4. The strain for use according to any of the embodiments 1-3, that is administered at a dose of 10<4> bacterial cells/day to 10<12> bacterial cells/day.

Embodiment 5. The strain for use according to the preceding embodiment, that is administered at a dose of 10<7> bacterial cells/day to 10<11> bacterial cells/day.

Embodiment 6. The strain for use according to the preceding embodiment, that is administered at a dose of 10<9> bacterial cells/day to 10<11> bacterial cells/day.

Embodiment 7. The strain for use according to the preceding embodiment, that is administered at a dose of 10<9> bacterial cells/day to 10<10> bacterial cells/day.

Embodiment 8. A composition comprising an effective amount of *Pediococcus acidilactici* strain for use in regulating blood glucose levels.

Embodiment 9. A composition comprising an effective amount of *Pediococcus acidilactici* strain for use in the prevention and/or treatment of hyperglycemia and/or a hyperglycemia-related condition.

Embodiment 10. The composition for use according to embodiment 9, wherein the oral composition reduces hyperglycemia in a subject by at least 50% relative to a control.

Embodiment 11. The composition for use according to embodiment 10, wherein the oral composition reduces hyperglycemia in a subject by at least 50% relative to as much as 120% relative to a control.

Embodiment 12. The composition for use according to any of the embodiments 10-11, wherein the oral composition reduces hyperglycemia in a subject by at least 55%.

Embodiment 13. The composition for use according to any of the embodiments 10-11, wherein the oral composition reduces hyperglycemia in a subject by at least 60%.

Embodiment 14. The composition for use according to any of the embodiments 10-11, wherein the oral composition reduces hyperglycemia in a subject by at least 65%.

Embodiment 15. The composition for use according to any of the embodiments 10-11, wherein the oral composition reduces hyperglycemia in a subject by at least 70%.

Embodiment 16. The composition for use according to any of the embodiments 10-11, wherein the oral composition reduces hyperglycemia in a subject by at least 75%.

Embodiment 17. The composition for use according to any of the embodiments 10-11, wherein the oral composition reduces hyperglycemia in a subject by at least 80%.

Embodiment 18. The composition for use according to any of the embodiments 10-11, wherein the oral composition reduces hyperglycemia in a subject to as much as 100%.

Embodiment 19. The composition for use according to any of the embodiments 10-18, wherein the control is the subject before being administered the composition or another subject suffering from hyperglycemia that is not administered the composition.

Embodiment 20. The composition for use according to any of the embodiments 9-18, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 21. The composition for use according to any of the embodiments 8-20, wherein the effective amount is from 10<4> to 10<12> bacterial cells/g or mL of the total composition.

Embodiment 22. The composition for use according to the preceding embodiment, wherein the effective amount is from 10<7> to 10<11> bacterial cells/g or mL of the total composition.

Embodiment 23. The composition for use according to the preceding embodiment, wherein the effective amount is from 10<9> to 10<11> bacterial cells/g or mL of the total composition.

Embodiment 24. The composition for use according to the preceding embodiment, wherein effective amount is from 10<9> to 10<10> bacterial cells/g or mL of the total composition.

Embodiment 25. The composition for use according to any of the embodiments 8-24, that is an oral composition Embodiment 26. The composition for use according to any of the embodiments 8-25, that is a pharmaceutical or nutraceutical composition and also comprises pharmaceutically acceptable excipients and carriers.

Embodiment 27. The composition for use according to embodiment 25, that is a food or feed product, a food or feed ingredient, a food or feed supplement or a nutraceutical product.

Embodiment 28. The composition for use according to the preceding embodiment, that is a functional food or feed product.

Embodiment 29. The strain for use according to any of the embodiments 1-7 or the composition for use according to any of the embodiments 8-28, that is for administering to subjects that have hyperglycemia or are at risk of having hyperglycemia.

Embodiment 30. The strain for use according to any of the embodiments 1-7 or the composition for use according to any of the embodiments 8-28, that is for administering to a prediabetic subject.

Embodiment 31. The strain for use according to any of the embodiments 1-7 or the composition for use according to any of the embodiments 8-28, that is for administering to a diabetic subject.

Embodiment 32. The strain for use according to any of the embodiments 1-7, 29-31, or the composition for use according to any of the embodiments 8-31, that is for administering to a mammal.

Embodiment 33. The strain or composition for use according to the preceding embodiment, wherein the mammal is a human.

Embodiment 34. The strain for use according to any of the embodiments 1-7, 29-31, or the composition for use according to any of the embodiments 8-31, that is for administering to a livestock animal.

Embodiment 35. The strain for use according to any of the embodiments 1-7, 29-34, or the composition for use according to any of the embodiments 8-34, wherein the strain or composition is for use in combination with at least one *Bacillus licheniformis* strain.

Embodiment 36. The strain or composition for use in combination according to the preceding embodiment, wherein the *Bacillus licheniformis* strain is *Bacillus licheniformis* deposited at the "Colección Española de Cultivos Tipo" (CECT) with identification reference CECT 9968.

Embodiment 37. The strain for use according to any of the embodiments 1-7, 29-36, or the composition for use according to any of the embodiments 8-36, wherein the strain or composition is for use in combination with a prebiotic.

Embodiment 38. The strain or composition for use in combination according to the preceding embodiment, wherein the prebiotic is selected from galacto-oligosaccharide (GOS), fructo-oligosaccharide (FOS), beta-glucans, inulin, and combinations thereof.

Embodiment 39. The strain for use according to any of the embodiments 1-7, 29-38, or the composition for use according to any of the embodiments 8-38, wherein the strain or composition is for use in combination with a further bioactive compound that contributes to the maintenance of normal blood glucose levels.

Embodiment 40. The strain or composition for use in combination according to the preceding embodiment, wherein the further bioactive compound that contributes to the maintenance of normal blood glucose levels is selected from sugar replacers, normoglycemic agents, drugs that control blood sugar levels and combinations thereof.

Embodiment 41. The strain or composition for use in combination according to any of the embodiments 35-40, wherein the combination is administered simultaneously, sequentially or within a therapeutically effective interval.

Embodiment 42. The composition for use according to any of the embodiments 8-41, wherein the composition further comprises a lubricating agent and or a bulking agent.

Embodiment 43. The composition for use according to the preceding embodiment, wherein the lubricating agent is magnesium stearate and the bulking agent is selected from starch, such as corn starch, cellulose, such as microcrystalline cellulose, and combinations thereof.

Embodiment 44. The composition for use according to any of the embodiments 8-43, wherein the composition further comprises an enteric coating.

Embodiment 45. The strain for use according to any of the embodiments 1-7, 29-38, or the composition for use according to any of the embodiments 8-44, wherein the regulating blood glucose levels comprises administering from 10<8> to 10<12> bacterial cells/day, in particular, from 10<9> to 10<10> bacterial cells/day.

Embodiment 46. The composition for use according to any of the embodiments 8-45, wherein the composition comprises a strain selected from *Pediococcus acidilactici* deposited at the "Colección Española de Cultivos Tipo" (CECT) with identification reference CECT 9879, the strain *Pediococcus acidilactici* deposited at the "Colección Española de Cultivos Tipo" (CECT) with identification reference CECT 9889, the strain *Pediococcus acidilactici* deposited at the "Colección Española de Cultivos Tipo" (CECT) with identification reference CECT 9967 and combinations thereof, and in particular the composition comprises the strain CECT 9879.

Embodiment 47. A strain of *Pediococcus acidilactici* deposited at the "Colección Española de Cultivos Tipo" (CECT) with identification reference CECT 9879.

Embodiment 48. A composition comprising an effective amount of a strain as defined in the preceding embodiment.

Embodiment 49. The composition according to the preceding embodiment, wherein the effective amount is from 10<4> to 10<12> bacterial cells/g or mL of the total composition.

Embodiment 50. The composition according to the preceding embodiment, wherein the effective amount is from 10<7> to 10<11> bacterial cells/g or mL of the total composition.

Embodiment 51. The composition according to the preceding embodiment, wherein the effective amount is from 10<9> to 10<11> bacterial cells/g or mL of the total composition.

Embodiment 52. The composition according to the preceding embodiment, wherein effective amount is from 10<9> to 10<10> bacterial cells/g or mL of the total composition.

Embodiment 53. The composition according to any of the embodiments 48-52, that is an oral composition.

Embodiment 54. The composition according to the preceding embodiment, that is a food or feed product, a food or feed ingredient, a food or feed supplement or a nutraceutical product.

Embodiment 55. The composition according to the preceding embodiment, that is a functional food or feed product.

Embodiment 56. The composition according to any of the embodiments 48-53, that is a pharmaceutical or nutraceutical composition and also comprises pharmaceutically acceptable excipients and carriers.

Embodiment 57. A strain as defined in embodiment 47 or a composition as defined in any of the embodiments 48-56 for use as probiotic.

Embodiment 58. A strain as defined in embodiment 47 or a composition as defined in any of the embodiments 48-56 for use as a medicament.

Embodiment 59. A strain as defined in embodiment 47 or a composition as defined in any of the embodiments 48-56 for use in regulating blood glucose levels.

Embodiment 60. A strain as defined in embodiment 47 or a composition as defined in any of the embodiments 48-56 for use in the prevention and/or treatment of hyperglycemia and/or a hyperglycemia-related condition.

Embodiment 61. The strain or composition for use according to the preceding claim, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 62. The strain or composition for use according to any of the embodiments 40-44, that is administered at a dose of 10<4> bacterial cells/day to 10<12> bacterial cells/day.

Embodiment 63. The strain or composition for use according to the preceding embodiment, that is administered at a dose of 10<7> bacterial cells/day to 10<11> bacterial cells/day.

Embodiment 64. The strain or composition for use according to the preceding embodiment, that is administered at a dose of 10<9> bacterial cells/day to 10<11> bacterial cells/day.

Embodiment 65. The strain or composition for use according to the preceding embodiment, that is administered at a dose of 10<9> bacterial cells/day to 10<10> bacterial cells/day.

Embodiment 66. The strain or composition for use according to any of the embodiments 57-65, that is for administering to subjects that have hyperglycemia or are at risk of having hyperglycemia.

Embodiment 67. The strain or composition for use according to any of the embodiments 57-65, that is for administering to a prediabetic subject.

Embodiment 68. The strain or composition for use according to any of the embodiments 57-65, that is for administering to a diabetic subject.

Embodiment 69. The strain or composition for use according to any of the embodiments 57-68, that is for administering to a mammal.

Embodiment 70. The strain or composition for use according to the preceding embodiment, wherein the mammal is a human.

Embodiment 71. The strain or composition for use according to any of the embodiments 57-68, that is for administering to a livestock animal.

Embodiment 72. The strain or composition for use according to any of the embodiments 57-71, wherein the strain or composition is for use in combination with at least one strain selected from a *Bacillus licheniformis* strain and a further *Pediococcus acidilactici* strain.

Embodiment 73. The strain or composition for use in combination according to the preceding embodiment, wherein the *Bacillus licheniformis* strain is *Bacillus licheniformis* deposited at the "Colección Española de Cultivos Tipo" (CECT) with identification reference CECT 9968, and the further *Pediococcus acidilactici* strain is *Pediococcus acidilactici* deposited at the "Colección Española de Cultivos Tipo" (CECT) with identification reference CECT 9889 or *Pediococcus acidilactici* deposited at the "Colección Española de Cultivos Tipo" (CECT) with identification reference CECT 9967.

Embodiment 74. The strain or composition for use according to any of the embodiments 57-73, wherein the strain or composition is for use in combination with a prebiotic.

Embodiment 75. The strain or composition for use according to any of the embodiments 57-74, wherein the strain or composition is for use in combination with an antidiabetic drug.

Embodiment 76. The strain or composition for use in combination according to any of the embodiments 71-75, wherein the combination is administered simultaneously, sequentially or within a therapeutically effective interval.

Embodiment 77. A strain of *Pediococcus acidilactici* deposited at the "Colección Española de Cultivos Tipo" (CECT) with identification reference CECT 9889.

Embodiment 78. A composition comprising an effective amount of a strain as defined in the preceding embodiment.

Embodiment 79. The composition according to the preceding embodiment, wherein the effective amount is from 10<4> to 10<12> bacterial cells/g or mL of the total composition.

Embodiment 80. The composition according to the preceding embodiment, wherein the effective amount is from 10<7> to 10<11> bacterial cells/g or mL of the total composition.

Embodiment 81. The composition according to the preceding embodiment, wherein the effective amount is from 10<9> to 10<11> bacterial cells/g or mL of the total composition.

Embodiment 82. The composition according to the preceding embodiment, wherein effective amount is from 10<9> to 10<10> bacterial cells/g or mL of the total composition.

Embodiment 83. The composition according to any of the embodiments 78-82, that is an oral composition.

Embodiment 84. The composition according to the preceding embodiment, that is a food or feed product, a food or feed ingredient, a food or feed supplement or a nutraceutical product.

Embodiment 85. The composition according to the preceding embodiment, that is a functional food or feed product.

Embodiment 86. The composition according to any of the embodiments 78-83, that is a pharmaceutical or nutraceutical composition and also comprises pharmaceutically acceptable excipients and carriers.

Embodiment 87. A strain as defined in embodiment 77 or a composition as defined in any of the embodiments 78-86 for use as probiotic.

Embodiment 88. A strain as defined in embodiment 77 or a composition as defined in any of the embodiments 78-86 for use as a medicament.

Embodiment 89. A strain as defined in embodiment 77 or a composition as defined in any of the embodiments 78-86 for use in regulating blood glucose levels.

Embodiment 90. A strain as defined in embodiment 77 or a composition as defined in any of the embodiments 78-86 for use in the prevention and/or treatment of hyperglycemia and/or a hyperglycemia-related condition.

Embodiment 91. The strain or composition for use according to the preceding claim, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 92. The strain or composition for use according to any of the embodiments 87-91, that is administered at a dose of 10<4> bacterial cells/day to 10<12> bacterial cells/day.

Embodiment 93. The strain or composition for use according to the preceding embodiment, that is administered at a dose of 10<7> bacterial cells/day to 10<11> bacterial cells/day.

Embodiment 94. The strain or composition for use according to the preceding embodiment, that is administered at a dose of 10<9> bacterial cells/day to 10<11> bacterial cells/day.

Embodiment 95. The strain or composition for use according to the preceding embodiment, that is administered at a dose of 10<9> bacterial cells/day to 10<10> bacterial cells/day.

Embodiment 96. The strain or composition for use according to any of the embodiments 87-95, that is for administering to subjects that have hyperglycemia or are at risk of having hyperglycemia.

Embodiment 97. The strain or composition for use according to any of the embodiments 87-95, that is for administering to a prediabetic subject.

Embodiment 98. The strain or composition for use according to any of the embodiments 87-95, that is for administering to a diabetic subject.

Embodiment 99. The strain or composition for use according to any of the embodiments 87-98, that is for administering to a mammal.

Embodiment 100. The strain or composition for use according to the preceding embodiment, wherein the mammal is a human.

Embodiment 101. The strain or composition for use according to any of the embodiments 87-98, that is for administering to a livestock animal.

Embodiment 102. The strain or composition for use according to any of the embodiments 87-101, wherein the strain or composition is for use in combination with at least one strain selected from a *Bacillus licheniformis* strain and a further *Pediococcus acidilactici* strain.

Embodiment 103. The strain or composition for use in combination according to the preceding embodiment, wherein *Bacillus licheniformis* strain is *Bacillus licheniformis* deposited at the "Colección Española de Cultivos Tipo" (CECT) with identification reference CECT 9968, and the further *Pediococcus acidilactici* strain is *Pediococcus acidilactici* deposited at the "Colección Española de Cultivos Tipo" (CECT) with identification reference CECT 9879 or

*Pediococcus acidilactici* deposited at the "Colección Española de Cultivos Tipo" (CECT) with identification reference CECT 9967.

Embodiment 104. The strain or composition for use according to any of the embodiments 87-103, wherein the strain or composition is for use in combination with a prebiotic.

Embodiment 105. The strain or composition for use according to any of the embodiments 87-104, wherein the strain or composition is for use in combination with an antidiabetic drug.

Embodiment 106. The strain or composition for use in combination according to any of the embodiments 102-105, wherein the combination is administered simultaneously, sequentially or within a therapeutically effective interval.

Embodiment 107. A strain of *Pediococcus acidilactici* deposited at the "Colección Española de Cultivos Tipo" (CECT) with identification reference CECT 9967.

Embodiment 108. A composition comprising an effective amount of a strain as defined in the preceding embodiment.

Embodiment 109. The composition according to the preceding embodiment, wherein the effective amount is from 10<4> to 10<12> bacterial cells/g or mL of the total composition.

Embodiment 110. The composition according to the preceding embodiment, wherein the effective amount is from 10<7> to 10<11> bacterial cells/g or mL of the total composition.

Embodiment 111. The composition according to the preceding embodiment, wherein the effective amount is from 10<9> to 10<11> bacterial cells/g or mL of the total composition.

Embodiment 112. The composition according to the preceding embodiment, wherein effective amount is from 10<9> to 10<10> bacterial cells/g or mL of the total composition.

Embodiment 113. The composition according to any of the embodiments 108-112, that is an oral composition.

Embodiment 114. The composition according to the preceding embodiment, that is a food or feed product, a food or feed ingredient, a food or feed supplement or a nutraceutical product.

Embodiment 115. The composition according to the preceding embodiment, that is a functional food or feed product.

Embodiment 116. The composition according to any of the embodiments 108-112, that is a pharmaceutical or nutraceutical composition and also comprises pharmaceutically acceptable excipients and carriers.

Embodiment 117. A strain as defined in embodiment 107 or a composition as defined in any of the embodiments 108-116 for use as probiotic.

Embodiment 118. A strain as defined in embodiment 107 or a composition as defined in any of the embodiments 108-116 for use as a medicament.

Embodiment 119. A strain as defined in embodiment 107 or a composition as defined in any of the embodiments 108-116 for use in regulating blood glucose levels.

Embodiment 120. A strain as defined in embodiment 107 or a composition as defined in any of the embodiments 108-116 for use in the prevention and/or treatment of hyperglycemia and/or a hyperglycemia-related condition.

Embodiment 121. The strain or composition for use according to the preceding claim, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 122. The strain or composition for use according to any of the embodiments 117-121, that is administered at a dose of 10<4> bacterial cells/day to 10<12> bacterial cells/day.

Embodiment 123. The strain or composition for use according to the preceding embodiment, that is administered at a dose of 10<7> bacterial cells/day to 10<11> bacterial cells/day.

Embodiment 124. The strain or composition for use according to the preceding embodiment, that is administered at a dose of 10<9> bacterial cells/day to 10<11> bacterial cells/day.

Embodiment 125. The strain or composition for use according to the preceding embodiment, that is administered at a dose of 10<9> bacterial cells/day to 10<10> bacterial cells/day.

Embodiment 126. The strain or composition for use according to any of the embodiments 117-125, that is for administering to subjects that have hyperglycemia or are at risk of having hyperglycemia.

Embodiment 127. The strain or composition for use according to any of the embodiments 117-125, that is for administering to a prediabetic subject.

Embodiment 128. The strain or composition for use according to any of the embodiments 117-125, that is for administering to a diabetic subject.

Embodiment 129. The strain or composition for use according to any of the embodiments 117-128, that is for administering to a mammal.

Embodiment 130. The strain or composition for use according to the preceding embodiment, wherein the mammal is a human.

Embodiment 131. The strain or composition for use according to any of the embodiments 117-128, that is for administering to a livestock animal.

Embodiment 132. The strain or composition for use according to any of the embodiments 117-131, wherein the strain or composition is for use in combination with at least one strain selected from a *Bacillus licheniformis* strain and a further *Pediococcus acidilactici* strain.

Embodiment 133. The strain or composition for use in combination according to the preceding embodiment, wherein the *Bacillus licheniformis* strain is *Bacillus licheniformis* deposited at the "Colección Española de Cultivos Tipo" (CECT) with identification reference CECT 9968, and the *Pediococcus acidilactici* strain is *Pediococcus acidilactici* deposited at the "Colección Española de Cultivos Tipo" (CECT) with identification reference CECT 9889 or *Pediococcus acidilactici* strain is *Pediococcus acidilactici* deposited at the "Colección Española de Cultivos Tipo" (CECT) with identification reference CECT 9879.

Embodiment 134. The strain or composition for use according to any of the embodiments 117-133, wherein the strain or composition is for use in combination with a prebiotic.

Embodiment 135. The strain or composition for use according to any of the embodiments 117-134, wherein the strain or composition is for use in combination with an antidiabetic drug.

Embodiment 136. The strain or composition for use in combination according to any of the embodiments 132-135, wherein the combination is administered simultaneously, sequentially or within a therapeutically effective interval.

Embodiment 137. A strain of *Bacillus licheniformis* deposited at the "Colección Española de Cultivos Tipo" (CECT) with identification reference CECT 9968.

Embodiment 138. A composition comprising an effective amount of a strain as defined in the preceding embodiment.

Embodiment 139. The composition according to the preceding embodiment, wherein the effective amount is from 10<4> to 10<12> bacterial cells/g or mL of the total composition.

Embodiment 140. The composition according to the preceding embodiment, wherein the effective amount is from 10<7> to 10<11> bacterial cells/g or mL of the total composition.

Embodiment 141. The composition according to the preceding embodiment, wherein the effective amount is from 10<9> to 10<11> bacterial cells/g or mL of the total composition.

Embodiment 142 The composition according to the preceding embodiment, wherein effective amount is from 10<9> to 10<10> bacterial cells/g or mL of the total composition.

Embodiment 143. The composition according to any of the embodiments 138-142, that is an oral composition.

Embodiment 144. The composition according to the preceding embodiment, that is a food or feed product, a food or feed ingredient, a food or feed supplement or a nutraceutical product.

Embodiment 145. The composition according to the preceding embodiment, that is a functional food or feed product.

Embodiment 146. The composition according to any of the embodiments 138-143, that is a pharmaceutical or nutraceutical composition and also comprises pharmaceutically acceptable excipients and carriers.

Embodiment 147. A strain as defined in embodiment 137 or a composition as defined in any of the embodiments 138-146 for use as probiotic.

Embodiment 148. A strain as defined in embodiment 137 or a composition as defined in any of the embodiments 138-146 for use as a medicament.

Embodiment 149. A strain as defined in embodiment 137 or a composition as defined in any of the embodiments 138-146 for use in regulating blood glucose levels.

Embodiment 150. A strain as defined in embodiment 137 or a composition as defined in any of the embodiments 138-146 for use in the prevention and/or treatment of hyperglycemia and/or a hyperglycemia-related condition.

Embodiment 151. The strain or oral composition for use according to the preceding claim, wherein the hyperglycemia-related condition is selected from impaired fasting glycemia (IFG), impaired glucose tolerance (IGT), postprandial hyperglycemia, glucose intolerance, insulin resistance, prediabetes, Type I diabetes, Type II diabetes, monogenic diabetes, neonatal diabetes mellitus, steroid diabetes and gestational diabetes.

Embodiment 152. The strain or composition for use according to any of the embodiments 147-151, that is administered at a dose of 10<4> bacterial cells/day to 10<12> bacterial cells/day.

Embodiment 153. The strain or composition for use according to the preceding embodiment, that is administered at a dose of 10<7> bacterial cells/day to 10<11> bacterial cells/day.

Embodiment 154. The strain or composition for use according to the preceding embodiment, that is administered at a dose of 10<9> bacterial cells/day to 10<11> bacterial cells/day.

Embodiment 155. The strain or composition for use according to the preceding embodiment, that is administered at a dose of 10<9> bacterial cells/day to 10<10> bacterial cells/day.

Embodiment 156. The strain or composition for use according to any of the embodiments 147-155, that is for administering to subjects that have hyperglycemia or are at risk of having hyperglycemia.

Embodiment 157. The strain or composition for use according to any of the embodiments 147-155, that is for administering to a prediabetic subject.

Embodiment 158. The strain or composition for use according to any of the embodiments 147-155, that is for administering to a diabetic subject.

Embodiment 159. The strain or composition for use according to any of the embodiments 147-158, that is for administering to a mammal.

Embodiment 160. The strain or composition for use according to the preceding embodiment, wherein the mammal is a human.

Embodiment 161. The strain or composition for use according to any of the embodiments 147-158, that is for administering to a livestock animal.

Embodiment 162. The strain or composition for use according to any of the embodiments 147-161, wherein the strain or composition is for use in combination with at least one strain of *Pediococcus acidilactici*.

Embodiment 163. The strain or composition for use in combination according to the preceding embodiment, wherein the *Pediococcus acidilactici* strain is selected from *Pediococcus acidilactici* deposited at the "Colección Española de Cultivos Tipo" (CECT) with identification reference CECT 9879, *Pediococcus acidilactici* deposited at the "Colección Española de Cultivos Tipo" (CECT) with identification reference CECT 9889, *Pediococcus acidilactici* deposited at the "Colección Española de Cultivos Tipo" (CECT) with identification reference CECT 9967 and combinations thereof.

Embodiment 164. The strain or composition for use according to any of the embodiments 147-163, wherein the strain or composition is for use in combination with a prebiotic.

Embodiment 165. The strain or composition for use according to any of the embodiments 147-164, wherein the strain or composition is for use in combination with an antidiabetic drug.

Embodiment 166. The strain or composition for use in combination according to any of the embodiments 162-165, wherein the combination is administered simultaneously, sequentially or within a therapeutically effective interval.

Embodiment 167. A method to obtain a mutant of a strain as defined in any of the embodiments 47, 77, 107 or 137, comprising the step of subjecting the defined in any of the embodiments 47, 77, 107 or 137 to a DNA recombinant technique or to conditions to generate spontaneous mutations.

Embodiment 168. The method according to the preceding embodiment, wherein the conditions to generate spontaneous mutations is exposure to UV light.

Embodiment 169. The method according to embodiment 167, wherein DNA recombinant technique is site directed mutagenesis.

Embodiment 170. A mutant obtained as defined in any of the embodiments 167-169.

Embodiment 171. The mutant according to the preceding embodiment which has above 99% DNA sequence identity along the full length of the genome with the original strain from which it derives and which retains the ability to regulate blood glucose levels of the strain from which it derives.

Embodiment 172. The mutant according to the preceding embodiment, wherein the identity is above 99.9%.

Embodiment 173. A culture's supernatant of a strain as defined in any of the embodiments 47, 77, 107 or 137.

Embodiment 174. The culture's supernatant according to the preceding embodiment which is obtainable by culturing the strain as defined in any of the embodiments 47, 77, 107 or 137 in an appropriate culture medium and conditions until reaching a bacterial cell density from 7×10<8> to 2×10<10> colony forming units (CFU)/mL or g substrate and removing the bacterial cells.

Embodiment 175. A cell free extract of a strain as defined in any of the embodiments 47, 77, 107 or 137.

Embodiment 176. The cell free extract according to the preceding embodiment which is obtainable by disrupting the strain as defined in any of the embodiments 47, 77, 107 or 137 and removing the cell wall and membrane components.

Embodiment 177. A metabolite having glucose levels-regulating effect derived from a strain as defined in any of the embodiments 47, 77, 107 or 137.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. NOD (Non-Obese Diabetic) Type 1 Diabetes Mouse Model 6 week-old NOD female mice were acquired, isolated during 4 weeks and used for the following studies.

1.1. Blood Glucose Control: Glucose Tolerance Test.

MATERIAL AND METHODS: Fasting glycaemia (12 h fasting) was determined in NOD female mice in a study performed for 40 weeks. Along this study, a glucose tolerance test (Andrikopoulos et al., 2008; Eyth et al., 2019) was performed determining the glycaemia at different timepoints (0, 5, 10, 15, 20, 25, 30, 35, 40, 50, 60 and 75 minutes) after administration of glucose (4 mg/kg) in mice subjected to standard diet (Ref 4rF21, Mucedola, Milan, Italy) (control, n=6) and mice on a standard diet supplemented with 2.4 g/day of an oral composition of *Pediococcus acidilactici* strain CECT 9879 (n=6). The oral composition contained 10<9> cfu of *Pediococcus acidilactici* strain CECT 9879/g of carrier. Independent experiments demonstrated that the carrier had no effect in the studied variables (results not shown). The oral composition of *Pediococcus acidilactici* strain CECT 9879 was consumed by the animals ad libitum. The daily dose corresponded to 75 mg bacteria/Kg mouse.

RESULTS: The administration of an oral composition containing *Pediococcus acidilactici* CECT 9879 is able to control blood glucose in the type 1 NOD diabetic mouse model. Mice that received the oral composition containing the strain *Pediococcus acidilactici* CECT 9879 showed blood glucose levels significantly lower than the control group (FIG. 1).

1.2. Blood Glucose Control: Survival Curve.

MATERIAL AND METHODS: Fasting glycaemia (12 h fasting) was determined in NOD female mice in a study performed for 40 weeks. Mice were divided into two experimental groups: one group was subjected to a normal diet (control group, n=21 NOD female mice) while the second group of mice was administered a standard diet supplemented with 2.4 g/day of oral composition of *Pediococcus acidilactici* strain CECT 9889 as described in example 1.1 (n=21 NOD female mice). Blood glucose levels were determined once per week. Diabetes debut was considered when mice showed fasting blood glucose levels greater than 350 mg/dl for at least three consecutive measurements.

Figure 2:
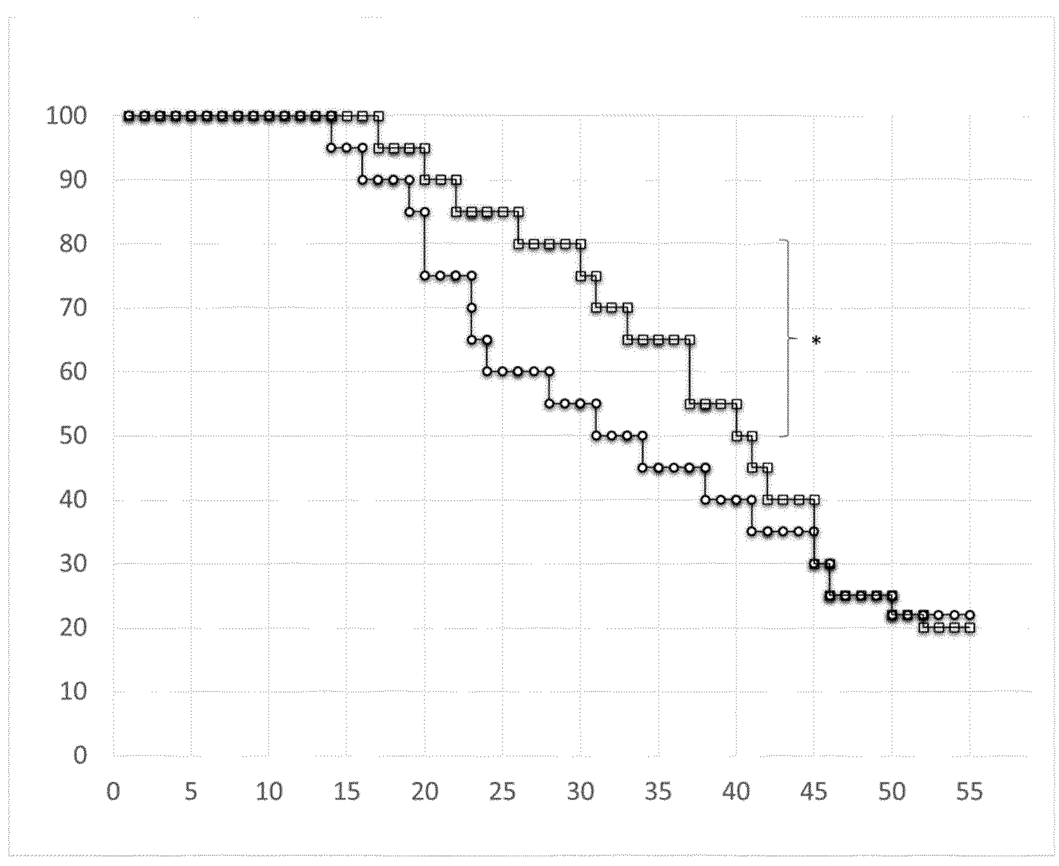
FIG. 2. NOD mice survival curve. The control group (line with circles, n=21 female NOD mice) showed an earlier debut in diabetes compared to the group whose diet was supplemented with *Pediococcus acidilactici* strain CECT 9879 (line with squares, n=21 female NOD mice). The ordinate axis (Y) indicates the percentage of disease-free mice and the abscissa axis (X) time (weeks). Values marked with an asterisk (*) indicate differences with a statistically significant p value (p<0.05).

RESULTS: The administration of an oral composition containing *Pediococcus acidilactici* CECT 9879 was able to delay the debut in diabetes (hyperglycemia) in type 1 diabetes mouse model NOD. The mice that received an oral composition containing the strain *Pediococcus acidilactici* CECT 9879 showed a significantly higher survival compared to the control group between weeks 20 and 40 of the study (FIG. 2).

Example 2. Results in Type 2 Diabetes ZDF (Zucker Diabetic and Fatty) Rat Model 6 week-old male ZDF rats were acquired, isolated during 4 weeks and used for the following studies.

2.1. Glycaemia, Ketone Bodies and Body Weight.

MATERIAL AND METHODS: Fasting blood glucose (12 h fasting) and body weight were determined in male ZDF rats in a 6 months experimental study. Animals were divided into two experimental groups: one group was subjected to a hypercaloric diet (Envigo, Ref. TD.06416) (control group, n=8) while the second group of ZDF rats was fed with a hypercaloric diet supplemented with 3.5 g/day of oral composition of *Pediococcus acidilactici* strain CECT 9879 as described in example 1.1 (n=8).

Figure 3:
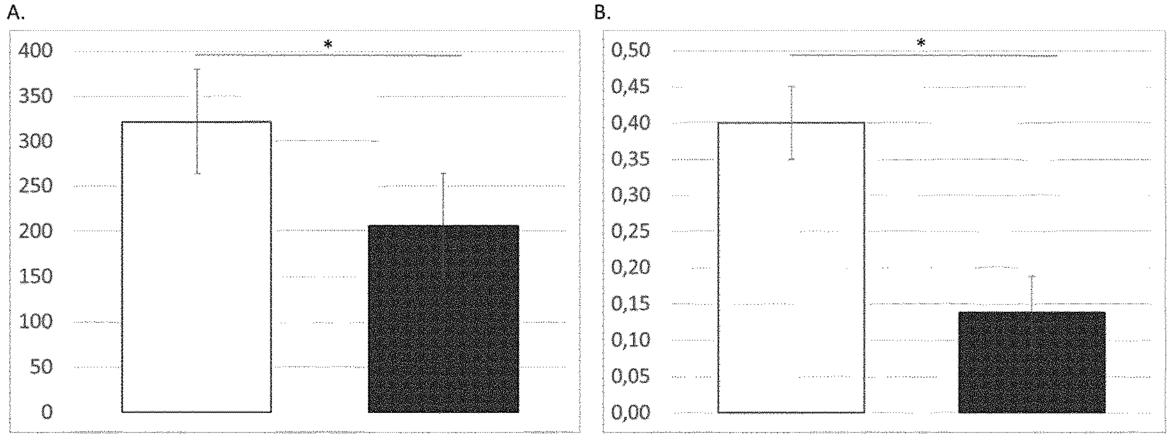
FIG. 3. Glycaemia (left panel, A) and ketone bodies (right panel, B) developed by the ZDF rats after 6 months of the experimental study. The control group (white bar on panel A, n=8 male ZDF rats) showed higher levels of blood glucose (panel A) and ketone bodies (panel B) in comparison with the group supplemented with *Pediococcus acidilactici* CECT 9879 (black bar on panel A and B, n=8 male ZDF rats). The ordinate axis (Y) in the left panel (A) indicates the blood glucose levels (mg/dL) whereas the ordinate axis (Y) in the right panel (B) indicates the blood ketone bodies levels (mmol/L). Values marked with an asterisk (*) indicate differences with a statistically significant p value (p<0.05).

RESULTS: The administration of an oral composition that includes the strain *Pediococcus acidilactici* CECT 9879 was able to delay the debut in diabetes (hyperglycemia) in the type 2 diabetic rat model ZDF (FIG. 3). In addition, the experimental groups fed the hypercaloric diet+oral composition containing *Pediococcus acidilactici* (n=8 rats/group) showed lower blood glucose levels.

In addition, the ZDF rats that received an oral composition containing the strain *Pediococcus acidilactici* CECT 9879 showed significantly lower levels of ketone bodies compared to the ZDF rats included in the control group. This result indicates a better glucose management, as it does not have to depend on the use of ketone bodies as an energy source.

Figure 4:
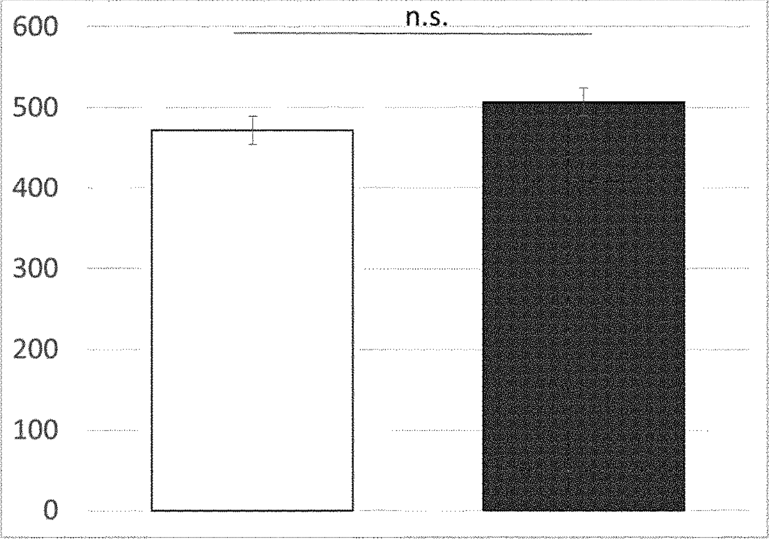
FIG. 4. Body weight determined in male ZDF rats at 6 months of the study. The control group (white bar, n=8 male ZDF rats) showed a similar body weight with respect to the group supplemented with *Pediococcus acidilactici* CECT 9879 (black bar, n=8 male ZDF rats). No significant differences (n.s.) were observed in the body weight of the rats at the end of the study. The ordinate axis (Y) in the panel indicates the weight (g), while the abscissa axis (X) represents the experimental groups performed.

Regarding the "body weight" variable, no significant differences were observed between the experimental groups (FIG. 4).

2.2. Glucose Tolerance Test.

MATERIAL AND METHODS Fasting blood glucose (12 h fasting) and body weight were determined in male ZDF rats in a 6 months experimental study. Animals were divided into two experimental groups: one group was subjected to a hypercaloric diet (Envigo, Ref. TD.06416) (control group, n=8) while the second group of ZDF rats was fed with a hypercaloric diet supplemented with 3.5 g/day of oral composition containing *Pediococcus acidilactici* strain CECT 9879 (n=8) as described in example 1.1. Along this study, a glucose tolerance test was performed determining the glycaemia at different timepoints (0, 20, 40, 60, 90, 120, 150 y 180 minutes) after administration of glucose (4 mg/kg) in ZDF rats subjected to hypercaloric diet (Envigo, Ref. TD.06416) or a hypercaloric diet supplemented with a product containing the *Pediococcus acidilactici* strain CECT 9879 (n=8).

Figure 5:
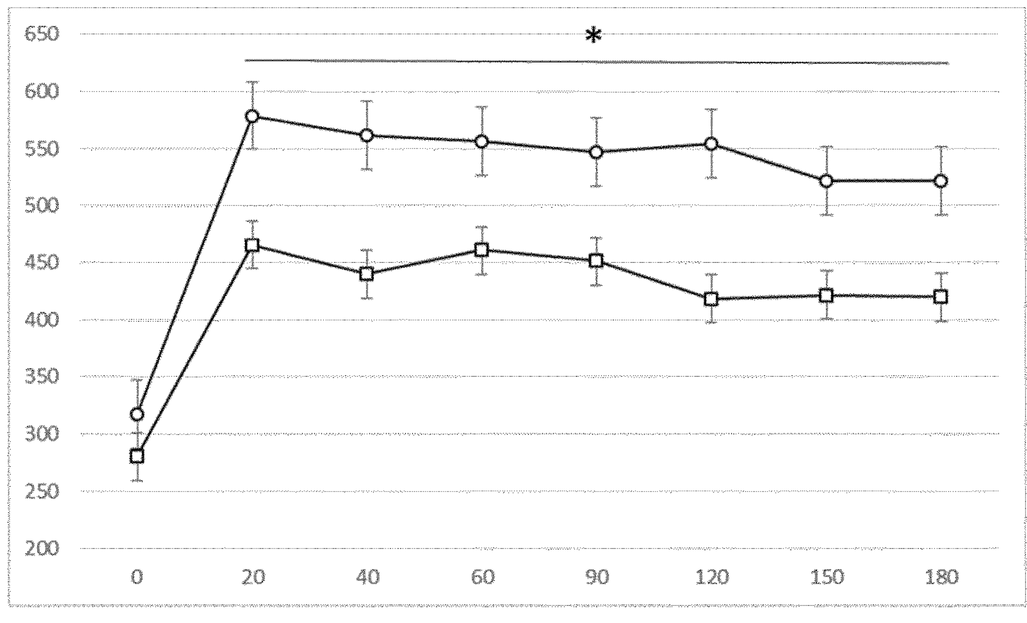
FIG. 5. Glucose tolerance test measured after 6 months study. The control group (line with circles, n=8 male ZDF rats) showed higher levels of blood glucose after the administration of 4 mg/kg of glucose with respect to the group supplemented with *Pediococcus acidilactici* CECT 9879 (line with squares, n=8 male ZDF rats). The ordinate axis (Y) represents the glycaemia (mg/dl) and the abscissa axis (X) the time (minutes). Values marked with an asterisk (*) indicate differences with a statistically significant p value (p<0.05).

RESULTS: The administration of an oral composition that includes the strain *Pediococcus acidilactici* CECT 9879 was able to control blood glucose in the type 2 diabetes ZDF rat model (FIG. 5). The ZDF rats that received the oral composition containing the strain *Pediococcus acidilactici* CECT 9879 showed significantly lower blood glucose levels compared to the control group.

2.3. Transaminases.

MATERIAL AND METHODS: Aspartate transaminase (AST) and alanine transaminase (ALT) were determined in 12 h fasting ZDF male rats in a 6 months experimental study. Animals were divided into two experimental groups: one group was subjected to a hypercaloric diet (Envigo, Ref. TD.06416) (control group, n=8) while the second group of ZDF rats was fed with a hypercaloric diet supplemented with 3.5 g/day of oral composition containing the *Pediococcus acidilactici* strain CECT 9879 as described in example 1.1 (n=8).

Figure 6:
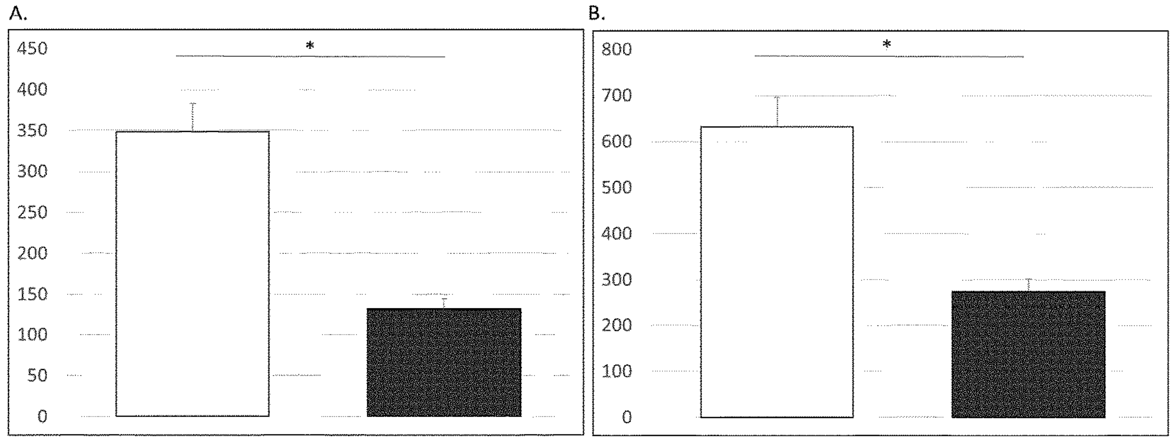
FIG. 6. AST (left panel (A)) and ALT values (right panel (B)) measured in ZDF rats at 6 months of the study. The control group (white bar in panel A and B, n=8 ZDF male rats) showed higher AST (panel A) and ALT (panel B) values in the control group compared with the group whose diet was supplemented with *Pediococcus acidilactici* CECT 9879 (black bar on panel A and B, n=8 ZDF male rats). The ordinate axis (Y) in the left panel (A) represents blood ALT levels (U/L). The ordinate axis (Y) in the right panel (B) indicates blood AST levels (U/L). Values marked with an asterisk (*) indicate differences with a statistically significant p value (p<0.05).

RESULTS: Rats that received an oral composition containing the strain *Pediococcus acidilactici* CECT 9879 showed significantly lower levels of transaminases AST and ALT in comparison with the ZDF rats included in the control group (FIG. 6). That result suggests a better hepatic functionality that results in better glycemic control, since the liver is one of the main organs involved in the control of blood glucose.

2.4. Survival.

MATERIAL AND METHODS: Survival was determined in male ZDF rats included in a 31 weeks experimental study. Animals were divided into two experimental groups: one group was subjected to a hypercaloric diet (Envigo, Ref. TD.06416) (control group, n=8) while the second group of ZDF rats was fed with a hypercaloric diet supplemented with 3.5 g/day of oral composition containing the *Pediococcus acidilactici* strain CECT 9879 as described in example 1.1 (n=8).

Figure 7:
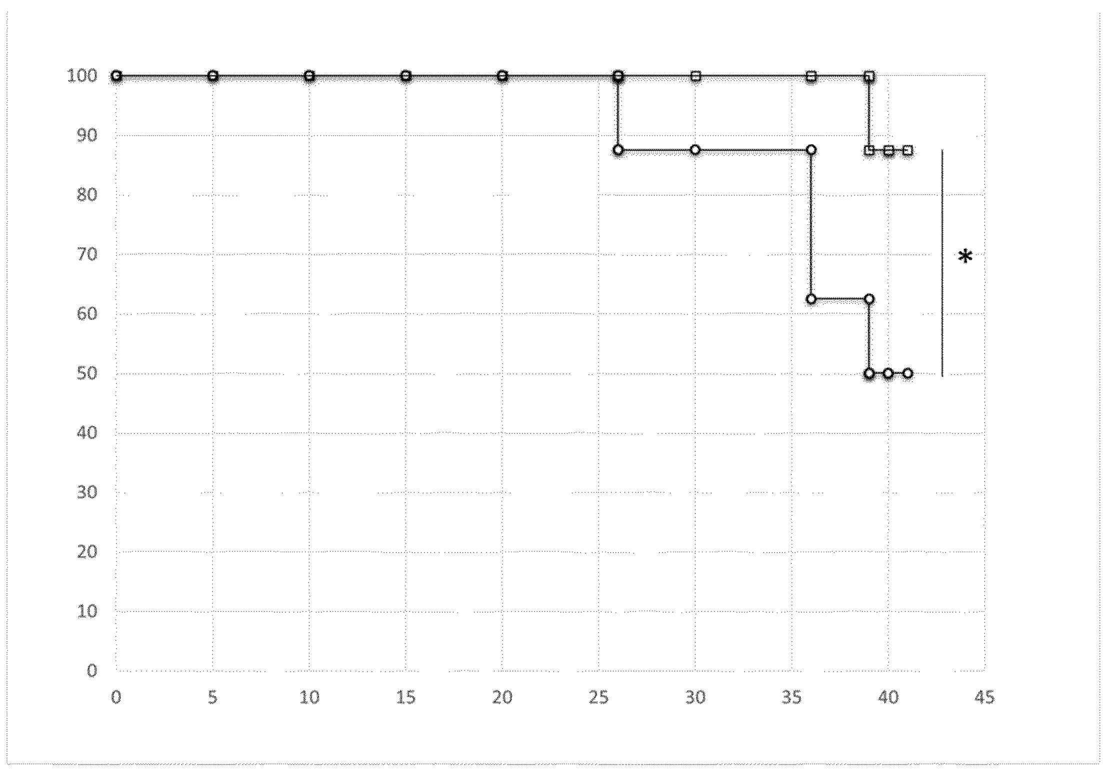
FIG. 7. Survival curve of ZDF rats. The control group (line with circles, n=8 male ZDF rats) showed an earlier debut in diabetes compared to the group supplemented with *Pediococcus acidilactici* strain CECT 9879 (line with squares, n=8 ZDF rats male). The ordinate axis (Y) indicates the percentage of disease free ZDF rats and the abscissa axis (X) time (weeks). Values marked with an asterisk (*) indicate differences with a statistically significant p value (p<0.05).

RESULTS: The administration of an oral composition that includes the strain *Pediococcus acidilactici* CECT 9879 was able to delay the debut in diabetes (hyperglycemia) in the ZDF type 2 diabetic rat model (FIG. 7). Rats that received the oral composition containing the strain *Pediococcus acidilactici* CECT 9879 showed a significantly higher survival compared to the control group between weeks 26 and 45 of the study. Regarding glycemic control, it is maintained over time. The results obtained during the 45 weeks that the study lasted demonstrate that the therapeutic effect did not decay during this period, indicating the stability of the oral composition that contains the *Pediococcus acidilactici* strain.

Example 3. Results in Balb/c Mouse-Induced Hiperglycemia by Hipercaloric Diet 9 week-old balb/c male mice were acquired, isolated during 4 weeks and used for the following study.

3.1. Effectiveness.

MATERIAL AND METHODS: Fasting glycaemia (12 h fasting) was determined in balb/c male mice in a study performed for 16 weeks. The mice were divided into two experimental groups: one group was fed with unsupplemented diet (control group, n=6) while the second group was supplemented with 2.4 g/day of oral composition containing the strain of *Pediococcus acidilactici* CECT 9879 as defined in example 1.1 (test group, n=6). The feeding schedule was as follows. All animals were fed a standard diet (Ref 4rF21, Mucedola, Milan, Italy) during the first 4 weeks and, after the fourth week, a hypercaloric diet (Envigo, Ref. TD.06416) until week 16. The test group was supplemented with the oral composition comprising *Pediococcus acidilactici* strain CECT 9879 except between week 8 and 12, when supplementation with was eliminated.

Figure 8:
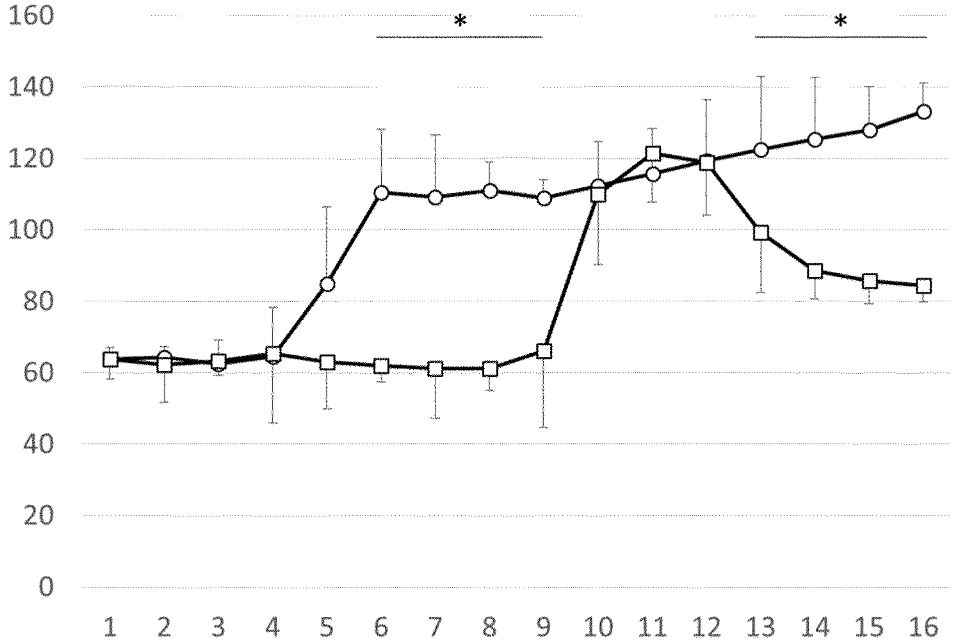
FIG. 8. Fasting blood glucose determinations. The control group (line with circles, n=6 male balb/c mice) showed higher blood glucose levels compared to the group supplemented with *Pediococcus acidilactici* strain CECT 9879 (line with squares, n=6 male balb/c mice) after administration of a hypercaloric diet from week 4 of the study. The elimination of the supplementation with *Pediococcus acidilactici* CECT 9879 from week 8 to week 12 increased the blood glucose levels in the group that had previously received the strain of *Pediococcus acidilactici* CECT 9879. The re-administration of this strain from week 12 induced a decrease in blood glucose. The ordinate axis (Y) represents the glycaemia (mg/dl) and the abscissa axis (X) the time (weeks). Values marked with an asterisk (*) indicate differences with a statistically significant p value (p<0.05).

RESULTS: The administration of an oral composition that includes the strain of *Pediococcus acidilactici* CECT 9879 was able to regulate glycaemia, being an effect dependent on the supplementation with this microorganism (FIG. 8). The withdrawal of this bacterium causes blood glucose levels to increase because of the hypercaloric diet. The readministration of the product that includes the strain of *Pediococcus acidilactici* CECT 9879 was able to reduce blood glucose levels again.

3.2. Significantly Higher Effect.

MATERIAL AND METHODS: Fasting glycaemia (12 h fasting) was determined in balb/c male mice in a study performed for 7 weeks. The mice were divided into four experimental groups: one group was fed with normal diet without *Pediococcus acidilactici* supplementation (control group, n=6) while the second (n=6), third (n=6) and fourth (n=6) groups were fed the normal diet supplemented with 2.4 g/day of oral composition of *Pediococcus acidilactici*. The oral composition contained carrier and 10<9> cfu of *Pediococcus acidilactici* CECT 9889, *Pediococcus acidilactici* CECT 9879 or *Pediococcus acidilactici* CECT 9967 for the second, third and fourth test groups, respectively. In all groups the normal diet (Ref 4rF21, Mucedola, Milan, Italy) was administered during the first 2 weeks and, after the second week, a hypercaloric diet (Envigo, Ref. TD.06416) was used until week 7.

Figure 9:
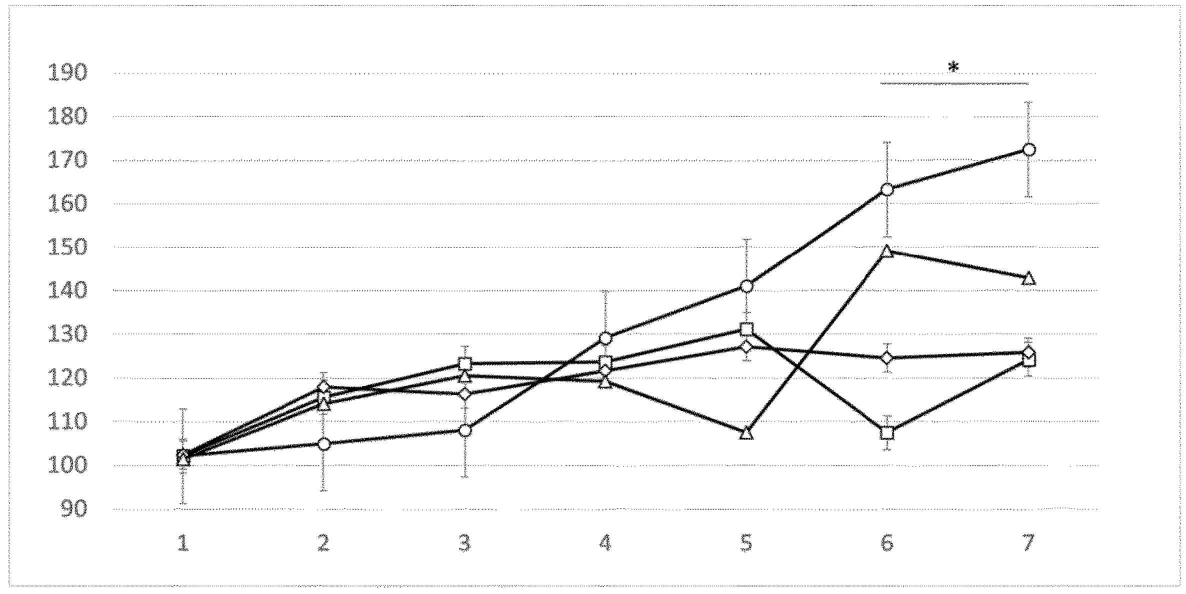
FIG. 9. Fasting blood glucose determinations. The control group (line with circles, n=6 male balb/c mice) showed higher blood glucose levels compared to the groups supplemented with *Pediococcus acidilactici* strain CECT 9889 (line with squares, n=6 male balb/c mice), *Pediococcus acidilactici* strain CECT 9867 (line with triangles, n=6 male balb/c mice) or *Pediococcus acidilactici* strain CECT 9879 (line with diamonds, n=6 male balb/c mice) after administration of a hypercaloric diet from week 2 of the study. The ordinate axis (Y) represents the glycaemia (mg/dl) and the abscissa axis (X) the time (weeks). Values marked with an asterisk (*) indicate differences with a statistically significant p value (p<0.05).

RESULTS: The administration of an oral compositions that include the strains of *Pediococcus acidilactici* of the invention were able to regulate the glycaemia after the stimulation of the hypercaloric diet (FIG. 9).

3.3. Supplementing with *Bacillus Licheniformis*

The effect of *B. licheniformis* strain CECT 9968 was studied by performing the experiment as described in 3.2 but substituting the oral composition of *Pediococcus acidilactici* by an oral composition which contained 10<9> cfu of *B. licheniformis* strain CECT 9968 and the carrier.

Figure 10:
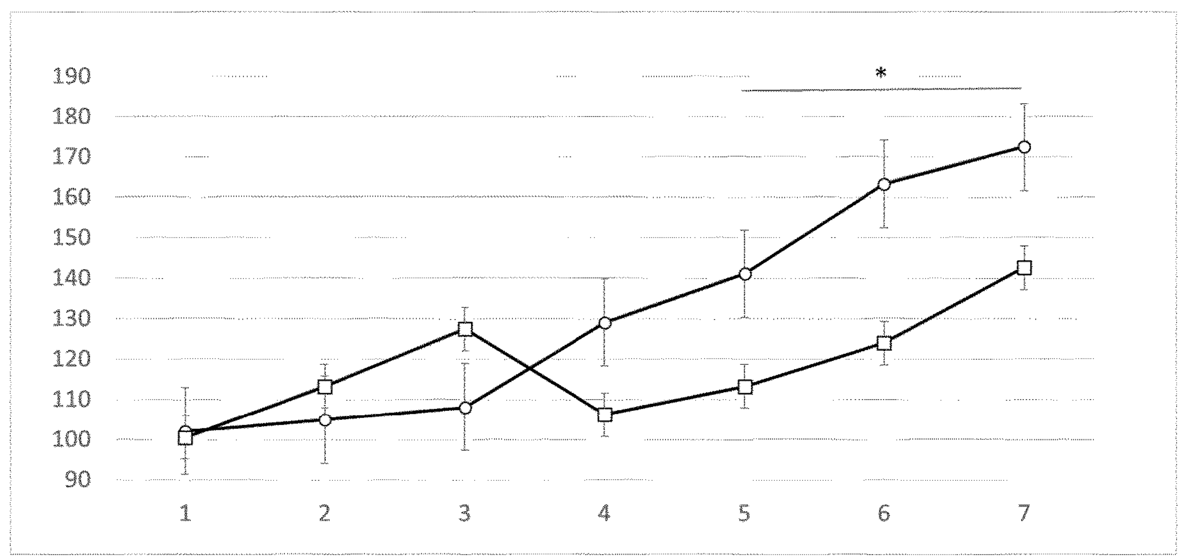
FIG. 10. Fasting blood glucose determinations. The control group (line with circles, n=6 male balb/c mice) showed higher blood glucose levels compared to the groups supplemented with *Bacillus licheniformis* strain CECT 9968 (line with squares, n=6 male balb/c mice) after administration of a hypercaloric diet from week 2 of the study. The ordinate axis (Y) represents the glycaemia (mg/dl) and the abscissa axis (X) the time (weeks). Values marked with an asterisk (*) indicate differences with a statistically significant p value (p<0.05).

Results show that administering an oral composition containing *B. licheniformis* strain CECT 9968 was able to regulate the glycaemia after the stimulation of the hypercaloric diet (FIG. 10).

3.4. Effect of Supplementing with Inactive *Pediococcus acidilactici*

The effect of inactivation of *Pediococcus acidilactici* strain CECT 9879 was studied by performing the experiment as described in 3.2 but inactivating the *Pediococcus acidilactici* CECT 9879 bacteria by autoclaving the oral composition. Administering an oral composition containing inactive *Pediococcus acidilactici* CECT 9879 was able to regulate the glycaemia after the stimulation of the hypercaloric diet to the same extend as the corresponding oral composition containing active *Pediococcus acidilactici* CECT 9879 (results not shown).

Example 4. Isolation, Identification and Culture Conditions of the Strains

Isolation: Strains were isolated from stool in dairy milk farms from Navarra region. Stool was taken from the rectum of different cows and refrigerated at +4° C. to transport immediately to the laboratory. 10 grams of each sample were mixed with 90 ml of buffered saline solution (PBS; pH 7.4), and stirred during 30 minutes. The suspension was used to prepare serial decimal dilutions in PBS. 100 microliters of each dilution were taken to culture on TSA standard medium, at 37° C. under aerobic conditions. The plates closed to 50 colonies were chosen as motherboard. Gram staining was carried out with all the strains in order to get a first identification. After that, all the colonies with different morphology were cultured individually in TSB standard (37° C. and aerobic conditions) during 48-72 hours depending on the strain, and after preserved frozen at −80° C. in a 1:1 mix of distilled water and glycerol.

Identification: From a new culture in a fresh plate from the frozen samples, a 0.5 McFarland bacterial suspension was prepared. DNA was extracted using the PureLink® Pro 96 Genomic DNA Purification Kit (Qiagen Inc., Chatsworth, California) following the manufacturer's instructions with a minor modification, which consisted in adding 140 μL of 10 mg/ml of lysozyme in Tris-EDTA buffer (pH 8.0) (Sigma Chemical Co., St. Louis, MO, USA) to the lysis buffer and incubating it at 37° C. during 30 minutes to improve the DNA extraction of Gram-positive bacteria. After elution from the column, 2 μL of Ribonuclease-A (Sigma Chemical Co., St. Louis, MO, USA) was added to eliminate residual RNA. Also, 4 μL of 0.8 μg/mL BSA (Sigma Chemical Co., St. Louis, MO, USA) was added to each sample. The DNA was stored at −20° C. until PCR amplification. PCR was performed with AmpliTaq Gold PCR-Master mix (Applied Biosystems, CA, USA) in a total reaction volume of 50 μL. The PCR mix consisted of 0.05 U/μL of AmpliTaq Gold polymerase, 0.8 μM per each primer, 0.1% of tween 20, 5 μL of template DNA (~100 ng), and autoclaved nanopure water. The 16S rDNA was amplified using the eubacterial primers: 357fm (5'-CTACGGGAGGCAGCAGT-3') and 907rm (5'-CCGTCWATTCMTTTGAGTTT-3') designed by Muyzer et al. (1993 and 1995).

In accordance with Sanger method, labelled dideoxyribonucleotide triphosphates (ddNTPs) together with unlabelled ones were used during DNA amplification.

The optimized conditions for amplification were as follows: activation of TaqGold at 94° C. (4 min), 35 cycles of denaturation at 94° C. (1 min), annealing at 45° C. (1 min) with an increment of 0.1° C. per cycle, extension at 72° C. (1 min 15 s), and a final extension at 72° C. (15 min). The obtained amplicons were examined by capillary electrophoresis and nucleotide sequences were examined using blastn with the GenBank database. Strains CECT 9889, CECT 9879 and CECT 9967 were identified by sequence identity as belonging to the species *Pediococcus acidilactici*. Strain CECT 9968 was identified as a *Bacillus licheniformis*. This identification was confirmed by complete genome sequencing in the Centre de Recerca en Sanitat Animal, Bellaterra (Barcelona-SPAIN).

Culture conditions: For all the experiments described above, cells of strains CECT 9889, CECT 9879, CECT 9967 and CECT 9968 were obtained by growing each strain in TSB standard medium at 37° C. and aerobic conditions for 48-72 h. Growth was stopped at exponential growth phase when the culture contained aprox. 109 microorganisms/ml and broth pH was 6+/−0.3. Bacterial cells were harvested by centrifugation and resuspended in distilled water; after that, the resuspended cells were mixed with a carrier to be used in the preparation of the oral composition.

Example 5. Stability and Thermal Resistance of *Pediococcus acidilactici* CECT 9879

Figure 11:
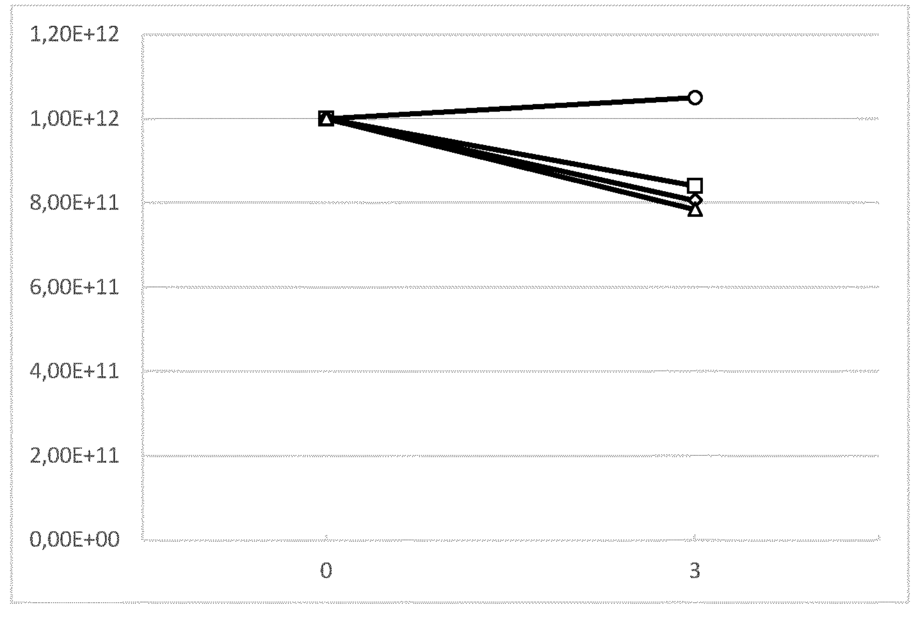
FIG. 11. Long term stability of *Pediococcus acidilactici* strain CECT 9879 concentrated probiotic powder. The strain at −20° C. (line with circles) showed higher stability at 3 months than the strain exposed to other conditions: +4° C.—Rh 35% (line with squares), +25° C.—Rh 60% (line with diamonds) and +30° C.—Rh 65% (line with triangles).

Samples of *Pediococcus acidilactici* CECT 9879 strain (lyophilized powder) were subjected to different storing conditions (−20° C., +4° C. with room humidity (Rh) 35%, +25° C. with Rh 60% and +30° C. with Rh 65%). Viability of the strain in the different samples was determined in MRS Agar at different times (0 and 3 months). FIG. 11 shows that *Pediococcus acidilactici* CECT 9879 suffers a slight loss of viability when stored during 3 months at 4° C.—Rh 35%, 25° C.—Rh 60% and 30° C.—Rh 65%. When stored at −20° C. the strain is perfectly stable.

Figure 12:
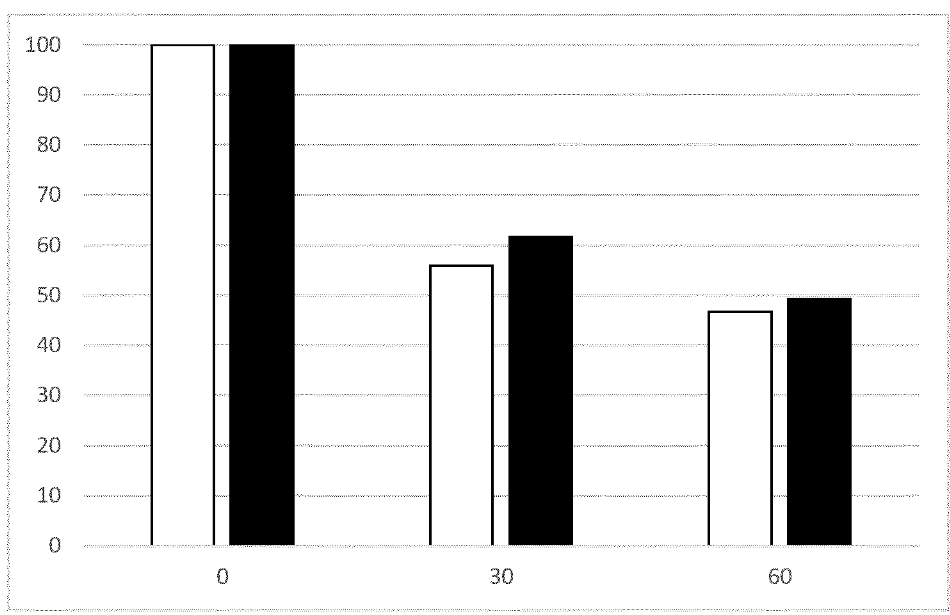
FIG. 12. Survival of the lyophilized *Pediococcus acidilactici* CECT 9879 strain and of a formulation containing *Pediococcus acidilactici* CECT 9879, exposed to a temperature of 78° C. Both samples show a survival close to 50% after 60 minutes of exposure to 78° C. The strain in the formulation (black bars) showed slightly higher survival levels than the strain alone (white bars). The ordinate axis (Y) represents the survival (%) and the abscissa axis (X) the time (minutes).

Resistance of the strain to high temperature was also studied. For this, samples of *Pediococcus acidilactici* CECT 9879 were placed in a stove at 78° C. and viability was determined in MRS Agar after 0, 30 and 60 minutes. FIG. 12 shows a survival close to 50% after 60 minutes of exposure to 78° C. for lyophilized *Pediococcus acidilactici* CECT 9879.

Example 6. Formulation

A formulation was prepared containing *Pediococcus acidilactici* CECT 9879 (10<9>-10<10>/g), microcrystalline cellulose, corn starch and magnesium stearate.

The thermal resistance of the strain in the formulation was also tested as described in example 6. As shown in FIG. 12, the strain in the formulation (black bars) showed slightly higher thermal resistance than the strain alone (white bars).

In vitro gastrointestinal resistance studies of the lyophilized *Pediococcus acidilactici* CECT 9879 strain and of the strain in the formulation were performed to assess its probiotic capacity. The simulated gastric fluid (SGF) pH: 1.2 and simulated intestinal fluid (SIF) pH: 6.8, with or without enzymes, were prepared according to the European Pharmacopoeia [EUROPEAN PHARMACOPOEIA 6.0. (2008). 2.9.3. Dissolution test for solid dosage forms. pp. 266-275.]. At least three individual replicates were performed per time and simulated medium. Viable counts of the strain were determined at 0, 30, 60 and 120 minutes by enumeration in MRS Agar after serial dilution.

Figure 13:
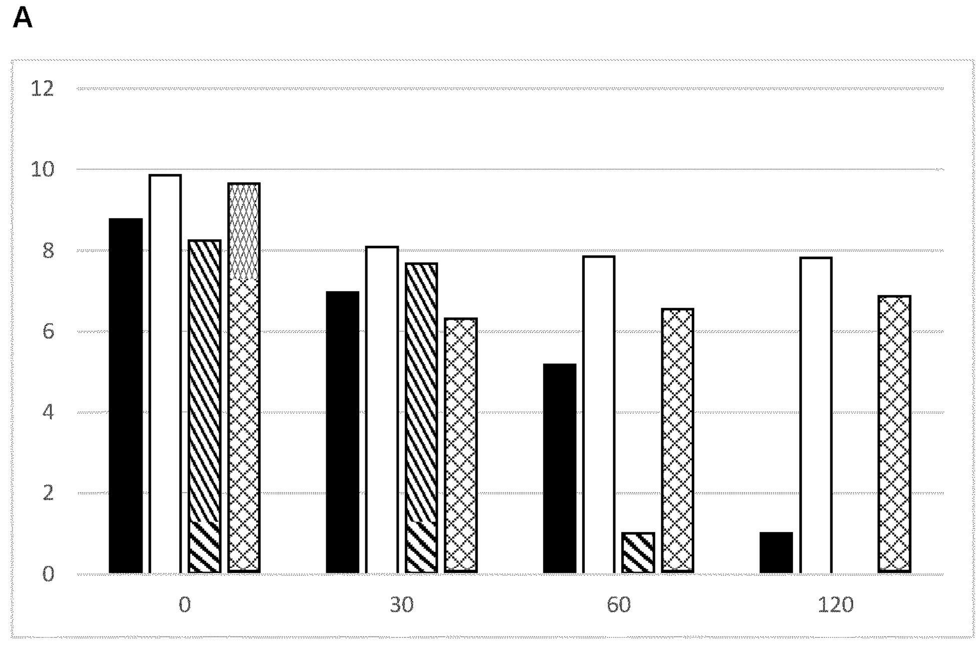
FIG. 13. A. Viability of the lyophilized *Pediococcus acidilactici* CECT 9879 strain and of the strain in the formulation, incubated in simulated gastric fluid (SGF), with or without enzymes. B. Viability of the lyophilized *Pediococcus acidilactici* CECT 9879 strain and of the strain in the formulation in simulated intestinal fluid (SIF), with or without enzymes. *Pediococcus acidilactici* strain without enzymes (black bars); *Pediococcus acidilactici* strain with enzymes (striped bars); *Pediococcus acidilactici* formulation without enzymes (white bars); *Pediococcus acidilactici* formulation in the presence of enzyme (diamond pattern bars). The ordinate axis (Y) represents the represents the counts (Log CFU/g) and the abscissa axis (X) the time (minutes).
Figure 13:
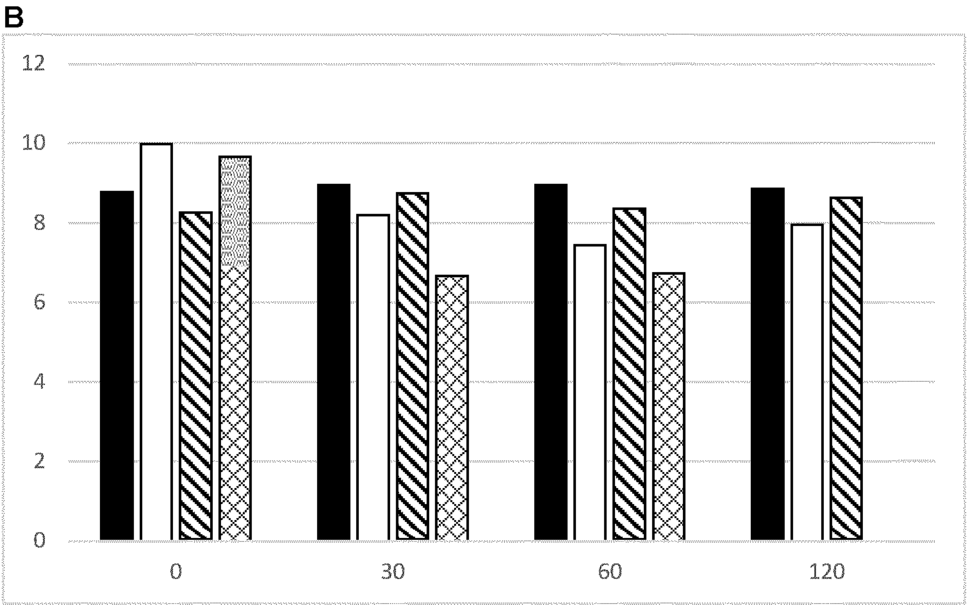

Results for gastrointestinal resistance are shown in FIG. 13. The survival of *Pediococcus acidilactici* strain is affected by the gastric environment without enzymes (black bars) and specially with enzymes (striped bars). The inclusion of the strain in the complete formulation offers a certain degree of protection against the action of acidic pH (white bars) and/or the presence of pepsin (diamond pattern bars). The simulated intestinal environment has no inhibitory effect on either the *Pediococcus acidilactici* CECT 9879 strain, with (striped bars) or without enzymes (black bars), or the strain in the formulation with (diamond pattern bars) or without enzymes (white bars).

The glucose regulating activity of the formulation was also studied in vivo. Fasting glycaemia (12 h fasting) was determined in 9 week-old balb/c male mice in a study performed for 6 weeks. The mice were divided into three experimental groups: one group was fed with un-supplemented diet (Control Group, n=12) while Group 1 and Group 2 were fed a diet supplemented with 2.4 g/day of the formulation. The feeding schedule was as follows. All animals were fed a standard diet (Ref 4rF21, Mucedola, Milan, Italy) during the first 2 weeks and, after the second week, a hypercaloric diet (Envigo, Ref. TD.06416) until week 6. Group 1 was supplemented with *Pediococcus acidilactici* CECT 9879 (lyophilized strain devoid excipients) while Group 2 was supplemented with the formulation, supplementation being performed along with both the normal diet and the hypercaloric diet.

Figure 14:
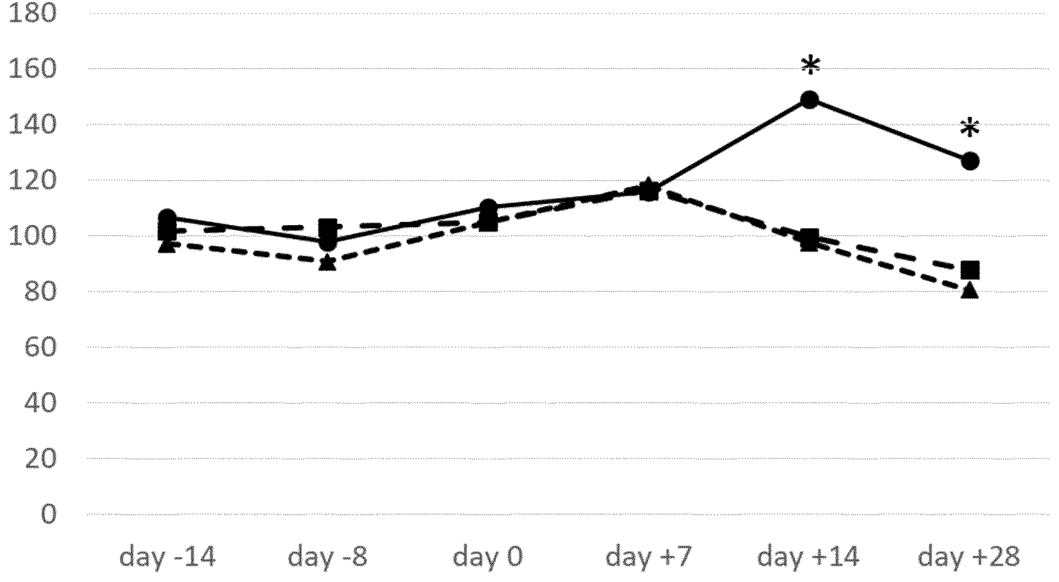
FIG. 14. Fasting blood glucose determinations. The control group (line with circles, n=12 male balb/c mice) showed higher blood glucose levels compared to the groups supplemented with *Pediococcus acidilactici* CECT 9879 (Groups 1 and 2) after administration of a hypercaloric diet from week 2 of the study (day 0). Group 1 was supplemented with *Pediococcus acidilactici* CECT 9879 without excipients (line with squares, n=12 male balb/c mice). Group 2 was supplemented with *Pediococcus acidilactici* CECT 9879 with excipients (line with triangles, n=12 male balb/c mice). The ordinate axis (Y) represents the glycaemia (mg/dl) and the abscissa axis (X) the time (days). Values marked with an asterisk (*) indicate differences with a statistically significant p value ($p<0.05$).

FIG. 14 shows that administration of *Pediococcus acidilactici* CECT 9879 (groups 1 and 2) was able to efficiently regulate glycaemia in comparison with the control group (which did not received *P. acidilactici* CECT 9879 supplement). No differences were observed between group 1 (and group 2, meaning that the excipients did not interfere with the glucose regulating activity of the strain.

CITATION LIST

Sambrook, J. and Russell, D W "Molecular Cloning: A Laboratory Manual", Chapter 13, "Mutagenesis", Cold Spring Harbor, 3rd Ed., 2001

Andrikopoulos S, Blair A R, Deluca N, Fam B C, Proietto J. (2008) Evaluating the glucose tolerance test in mice. Am J Physiol Endocrinol Metab; 295(6): E1323-32. doi: 10.1152/ajpendo.90617.2008.

Eyth E, Basit H, Smith C J. Glucose Tolerance Test. [Updated 2019 Jun. 1]. In: StatPearls Treasure Island (FL): StatPearls Publishing.

ADA Standards of Medical Care Diabetes Care 2019 January; 42 (Supplement 1): S1-S2.

Pharmacologic Approaches to Glycemic Treatment: Standards of Medical Care in Diabetes-2019; American Diabetes Association. Diabetes Care 2019 January; 42 (Supplement 1): S90-S102.

Muyzer G, de Waal E C, Uitterlinden A G. Profiling of complex microbial populations by denaturing gradient gel electrophoresis analysis of polymerase chain reaction-amplified genes coding for 16S rRNA. Appl Environ Microbiol. 1993 March; 59(3):695-700.

Muyzer G, Teske A, Wirsen C O, Jannasch H W. Phylogenetic relationships of Thiomicrospira species and their identification in deep-sea hydrothermal vent samples by denaturing gradient gel electrophoresis of 16S rDNA fragments. Arch Microbiol. 1995 September; 164(3):165-72.

EUROPEAN PHARMACOPOEIA 6.0. (2008). 2.9.3. Dissolution test for solid dosage forms. pp. 266-275.

The invention claimed is:

1. A method for regulating blood glucose levels in an animal in need thereof comprising orally administering to said animal an effective amount of *Pediococcus acidilactici* CECT 9879, wherein the effective amount is $10^4$ to $10^{12}$ bacteria per dose, per day, or per 24-hour period.

2. The method according to claim 1, further comprising administering to the animal a compound that contributes to the maintenance of normal blood glucose levels.

3. The method according to claim 2, wherein the compound that contributes to the maintenance of normal blood glucose levels is selected from sugar replacers, normoglycemic agents, drugs that control blood sugar levels and combinations thereof.

4. The method according to claim 2, wherein the compound that contributes to the maintenance of normal blood glucose levels is selected from the group consisting of Chromium, beta-glucan, metformin, and combinations thereof.

5. The method according to claim 2, wherein the *Pediococcus acidilactici* CECT 9879 and the compound that contributes to the maintenance of normal blood glucose levels are administered simultaneously or sequentially.

6. A method for the prevention and/or treatment of hyperglycemia and/or a hyperglycemia-related condition selected from the group consisting of impaired fasting glycemia (IFG), impaired glucose tolerance (IGT), postprandial hyperglycemia, glucose intolerance, Type II pre-diabetes, and gestational diabetes in an animal in need thereof, the method comprising orally administering to said animal an effective amount of *Pediococcus acidilactici* CECT 9879, wherein the effective amount is $10^4$ to $10^{12}$ bacteria per dose, per day, or per 24-hour period.

7. The method according to claim 6, wherein the *Pediococcus acidilactici* CECT 9879 is administered to a prediabetic animal.

8. The method according to claim 1, wherein the *Pediococcus acidilactici* CECT 9879 is non-viable.

* * * * *